(12) United States Patent
Zhou et al.

(10) Patent No.: US 12,384,774 B2
(45) Date of Patent: Aug. 12, 2025

(54) POLYMORPH OF CDK9 INHIBITOR AND PREPARATION METHOD FOR POLYMORPH AND USE THEREOF

(71) Applicants: GenFleet Therapeutics (Shanghai) Inc., Shanghai (CN); Zhejiang Genfleet Therapeutics Co., Ltd., Zhejiang (CN)

(72) Inventors: Fusheng Zhou, Shanghai (CN); Jinzhu Zhao, Shanghai (CN); Jiong Lan, Shanghai (CN)

(73) Assignees: GenFleet Therapeutics (Shanghai) Inc., Shanghai (CN); Zhejiang Genfleet Therapeutics Co., Ltd., Zhejiang (CN)

( * ) Notice: Subject to any disclaimer, the term of this patent is extended or adjusted under 35 U.S.C. 154(b) by 852 days.

(21) Appl. No.: 17/596,227

(22) PCT Filed: Jun. 5, 2020

(86) PCT No.: PCT/CN2020/094527
§ 371 (c)(1),
(2) Date: Dec. 6, 2021

(87) PCT Pub. No.: WO2020/244612
PCT Pub. Date: Dec. 10, 2020

(65) Prior Publication Data
US 2022/0315576 A1   Oct. 6, 2022

(30) Foreign Application Priority Data
Jun. 6, 2019 (CN) .......................... 201910489946.1

(51) Int. Cl.
*C07D 417/14* (2006.01)
*A61P 35/00* (2006.01)

(52) U.S. Cl.
CPC ............ *C07D 417/14* (2013.01); *A61P 35/00* (2018.01); *C07B 2200/13* (2013.01)

(58) Field of Classification Search
CPC .... C07D 417/14; A61P 35/00; C07B 2200/13
(Continued)

(56) References Cited

U.S. PATENT DOCUMENTS 7,851,476 B2   12/2010   Chen et al.
10,952,999 B2 *  3/2021   Zhou .................... A61K 31/443
2020/0078343 A1   3/2020   Zhou

FOREIGN PATENT DOCUMENTS

CA   3059622 A1   10/2018
CN   108727363 A   11/2018
(Continued)

OTHER PUBLICATIONS

Examination Report No. 2 in Australian Application No. 2020288270 (May 2023).
(Continued)

*Primary Examiner* — Jeffrey S Lundgren
*Assistant Examiner* — Heather Dahlin

(57) ABSTRACT

The present invention provides a polymorph of a CDK9 inhibitor and a preparation method for the polymorph and use thereof. Specifically, disclosed are 4-(((4-(5-chloro-2-(((1R,4r)-4-(((R)-1-methoxypropyl-2-yl)amino)cyclohexyl)amino)pyridine-4-yl)thiazole-2-yl)amino)methyl)tetrahydro-2H-pyrano-4-methylnitrile maleate or fumarate or polymorphs thereof and applications thereof. In addition, also disclosed are a pharmaceutical composition containing the substance and an application of the pharmaceutical composition.

21 Claims, 10 Drawing Sheets

(58) Field of Classification Search
USPC .......................................................... 514/342
See application file for complete search history.

(56) References Cited

FOREIGN PATENT DOCUMENTS

| EA | 014706 B1 | 2/2011 |
|----|-----------|--------|
| EP | 3 613 737 A1 | 2/2020 |
| JP | 2003-519698 A | 6/2003 |
| JP | 2013-542967 A | 11/2013 |
| JP | 2014-520824 A | 8/2014 |
| WO | 01/51919 A2 | 7/2001 |
| WO | 2012/066070 A1 | 5/2012 |
| WO | 2013/010679 A1 | 1/2013 |

OTHER PUBLICATIONS

Decision to Grant a Patent in Japanese Application No. 2021-572289 (Jul. 2023).
International Search Report and Written Opinion in International Application No. PCT/CN2020/094527 (Sep. 2020).
Robert J. Sims III et al., "Elongation by RNA Polymerase II: The Short and Long of It," 18(20) Genes Dev. 2437-2468 (Oct. 2004).
Yuki Yamaguchi et al., "Evidence that Negative Elongation Factor Represses Transcription Elongation through Binding to a DRB Sensitivity-Inducing Factor/RNA Polymerase II Complex and RNA," 22(9) Mol. Cell Biol. 2918-2927 (May 2002).
Examination Report No. 1 in Australian Application No. 2020288270 (Sep. 2022).
Dharmendra Singhal et al., "Drug Polymorphism and Dosage Form Design: A Practical Perspective," 56 Adv. Drug Deliv. Rev. 335-347 (2004).
Mino R. Caira, "Crystalline Polymorphism of Organic Compounds," Design of Organic Solids (Topics in Current Chemistry, 198), E. Weber E et al. (ed), pp. 163-208 (1998).
Stefan Balbach et al., Pharmaceutical Evaluation of Early Development Candidates, 'The 100 mg Approach', 275 Int. J. Pharm., 1-12 (2004).
International Search Report (with English translation) and Written Opinion issued in PCT/CN2020/094527, dated Sep. 10, 2020, 8 pages provided.
Sims et al., "Elongation by RNA polymerase II: the short and long of it", downloaded from genesdev.cshlp.org on Nov. 19, 2021, Published by Cold Spring Harbor Laboratory Press, 33 pages provided.
Yamaguchi et al., "Evidence that negative elongation factor represses transcription elongation through binding to a DRB sensitivity-inducing factor/RNA polymerase II complex and RNA", Mol Cell Biol, May 2002, vol. 22 No. 9, pp. 2918-2927.
Examiner Requisition in Canadian Application No. 3,142,444 (Dec. 2022).
Office Action in Eurasian Application No. 202293393 (Nov. 2023).
Extended European Search Report in European Application No. 20819010.8 (Jun. 2016).
Beilei Wang et al., "Discovery of 4-(((4-(5-chloro-2-(((1s,4s)-4-((2-methoxyethyl)amino)cyclohexyl)amino)pyridin-4-yl) thiazol-2-yl)amino)methyl)tetrahydro-2H-pyran-4-carbonitrile (JSH-150) as a Novel Highly Selective and Potent CDK9 Kinase Inhibitor," 158(1) Eur. J. Med. Chem. 896-916 (2018) (XP055714086).
Notice of Reason for Rejection in Korean Application No. 10-2022-7000035 (Feb. 2024).
Barbara Rodriguez-Spong et al.. "General Principles of Pharmaceutical Solid Polymorphism: A Supramolecular Perspective", 56 Adv. Drug Deliv. Rev. 241-274 (2004).
Sherry L. Morissette et al., "High-Throughput Crystallization: Polymorphs, Salts, Co-Crystals and Solvates of Pharmaceutical Solids," 56 Adv. Drug Deliv. Rev. 275-300 (2004).
Richard J. Bastin et al., "Salt Selection and Optimisation Procedures for Pharmaceutical New Chemical Entities," 4 Org. Process Res. Dev. 427-435 (2000).
Klaus Kümmerer, "Pharmaceuticals in the Environment," 35 Annu. Rev. Environ. Resour. 57-75, (2010).
Office Action in Russian Application No. 2021139907 (Oct. 2022).
Joel Bernstein, "Polymorphism in Molecular Crystals," Ch. 7.3.2.: Bioavailability, pp. 324-330 Moscow, Nauka (2007), Portion cited in Russian OC.
Joel Bernstein, "Polymorphism in Molecular Crystals," 1st ed., Ch. 7.3.2.: Bioavailability, pp. 244-249 (2002), Portion cited in Russian OC.
G.A. Kuznetsova, "Qualitative X-Ray Phase Analysis: Guidelines," Introduction, pp. 2-3, Irkutsk State University (Govpoigu), Department of General Physics (2005), Portion cited in Russian OC.
Notice of Reasons for Refusal in Japanese Application No. 2021-572289 (Dec. 2022).
Yoko Kawaguchi et al., "Drug and Crystal Polymorphism," 4(2) Biotechnol. Res., J. Hum. Environ. Eng. 310-317 (2002).
Noriyuki Takada, "API Form Screening and Selection in Drug Discovery Stage," 6(10) Pharm Stage 20-25 (2007).

* cited by examiner

POLYMORPH OF CDK9 INHIBITOR AND PREPARATION METHOD FOR POLYMORPH AND USE THEREOF

TECHNICAL FIELD

The present invention relates to the medical technical field, and specifically relates to a polymorph of a CDK9 inhibitor and the preparation method therefor and use thereof.

BACKGROUND

The proliferation and division of eukaryotic cells is a precise and complex regulation process. The process of proliferation is completed through cell cycle, and the orderly progress of the cell cycle is completed through its strict molecular regulation mechanisms. At present, it has been discovered that there are three main types of molecules involved in regulation of the cell cycle: cyclin-dependent kinases (CDK), cyclins, and cyclin-dependent kinase inhibitors, CKI), in which CDK plays an important role. It has been found that the CDK family has 13 members (CDK1-CDK13), which are divided into two categories according to their intracellular functions: CDK that controls the cell cycle and CDK that controls cell transcription. CDK9 belongs to the serine kinases. The complex formed by combining it with the corresponding cyclin is called positive transcription elongation factor b (P-TEFb), which can phosphorylate RNA polymerase II (RNA polymerase II) and some negative transcription elongation factors (NELF and N-TEF), which extend transcription from the starting site, and are the core molecules that extend transcription (Sims RJ 3rd et al. Genes Dev, 2004, 18: 2437-68; Yamaguchi Y et al. Mol Cell Biol, 2002, 22: 2918-27). Studies have found that abnormalities in the expression level of CDK9 or/and kinase activity can cause abnormalities in the expression of multiple proteins or/and their mRNA levels in cells. It has been proven that tumors are closely related to anti-apoptotic proteins (such as Bcl-2), cell cycle-related regulatory proteins (such as cyclin D1), p53 pathway-related proteins, certain proteins of the NF-κB pathway, tumor microenvironment related proteins (such as VEGF) and so on. It can be seen that CDK9 is one of the most critical molecules in the development of tumors.

Therefore, the development of medicine to regulate CDK9 is essential for the prevention and treatment of diseases related to CDK9.

SUMMARY OF INVENTION

The purpose of the present invention is to provide a class of CDK9 inhibitors that are more stable and more suitable for medicine. Specifically, the purpose of the present invention is to provide salts of compound 4-(((4-(5-chloro-2-(((1R,4r)-4-(((R)-1-methoxypropyl-2-yl)amino)cyclohexyl)amino)pyridin-4-yl)thiazol-2-yl)amino)methyl)tetrahydro-2H-pyran-4-carbonitrile and a series of stable polymorphs thereof preparation methods for the polymorphs and uses of the polymorphs mentioned above.

In the first aspect, the present invention provides a pharmaceutically acceptable salt of the compound of formula (I) or a polymorph thereof;

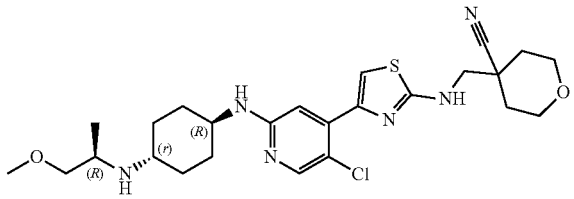

the pharmaceutically acceptable salt is a maleate or a fumarate.

In another preferred embodiment, the pharmaceutically acceptable salt of the compound of formula (I) is the maleate of the compound of formula (I).

In another preferred embodiment, the pharmaceutically acceptable salt of the compound of formula (I) is the fumarate of the compound of formula (I).

In another preferred embodiment, in the maleate of the compound of formula (I), the molar ratio of the compound of formula (I) to maleic acid is 1:2.

In another preferred embodiment, in the fumarate of the compound of formula (I), the molar ratio of the compound of formula (I) to fumaric acid is 2:1.

In another preferred embodiment, the polymorph is crystal form 1 of the maleate of the compound of formula (I), and the X-ray powder diffraction pattern of the crystal form 1 comprises the diffraction angle 2θ(°) values selected from the following group: 5.48±0.2°, 14.26±0.2°, 19.68±0.2°, 22.44±0.2°.

In another preferred embodiment, the X-ray powder diffraction pattern of the crystal form 1 further comprises one or more (for example, 2, 3, 4, 5, 6, 7, 8, 9, 10, 11, 12, 13, 14 or all) diffraction angle 2θ(°) values selected from the following group: 5.02±0.2°, 9.86±0.2°, 10.88±0.2°, 11.22±0.2°, 15.06±0.2°, 16.82±0.2°, 17.48±0.2°, 18.18±0.2°, 20.50±0.2°, 23.24±0.2°, 24.90±0.2°, 26.76±0.2°, 27.16±0.2°, 28.48±0.2°, 30.86±0.2°.

In another preferred embodiment, the X-ray powder diffraction pattern of the crystal form 1 further comprises diffraction angle 2θ (°) values selected from the following group: 9.86±0.2°, 11.22±0.2°, 15.06±0.2°, 23.24±0.2°, 24.90±0.2°.

In another preferred embodiment, the X-ray powder diffraction pattern of the crystal form 1 further comprises diffraction angle 2θ (°) values selected from the following group: 5.02±0.2°, 16.82±0.2°, 26.76±0.2°, 27.16±0.2°.

In another preferred embodiment, the X-ray powder diffraction pattern of the crystal form 1 further comprises diffraction angle 2θ (°) values selected from the following group: 18.18±0.2°, 20.50±0.2°.

In another preferred embodiment, the X-ray powder diffraction pattern of the crystal form 1 further comprises one or more (for example, 2, 3, 4, 5, 6, 7, 8, 9, more or all) diffraction angle 2θ (°) values selected from table 2.

In another preferred embodiment, the X-ray powder diffraction pattern of the crystal form 1 is basically as shown in FIG. 1.

In another preferred embodiment, the differential scanning calorimetry analysis spectrum of the crystal form 1 has a characteristic peak at 162.45±5° C.

In another preferred embodiment, the differential scanning calorimetry analysis spectrum of the crystal form 1 has a characteristic peak at 162.45±2° C. (or 162.45±1° C.).

In another preferred embodiment, the differential scanning calorimetry analysis spectrum of the crystal form 1 is basically as shown in FIG. 2.

In another preferred embodiment, the thermogravimetric analysis spectrum of the crystal form 1 has characteristic peaks at 179.19±5° C. and 366.44±5° C.

In another preferred embodiment, the thermogravimetric analysis spectrum of the crystal form 1 has characteristic peaks at 179.19±2° C. and 366.44±2° C.

In another preferred embodiment, the thermogravimetric analysis spectrum of the crystal form 1 is basically as shown in FIG. 3.

In another preferred embodiment, the infrared spectrum of the crystal form 1 has characteristic peaks at the following positions: 3423.90±5 cm$^{-1}$, 2956.16±5 cm$^{-1}$, 2854.93±5 cm$^{-1}$, 1647.45±5 cm$^{-1}$, 1565.70±5 cm$^{-1}$, 1491.36±5 cm$^{-1}$, 1384.83±5 cm$^{-1}$, 1365.96±5 cm$^{-1}$, 1179.36±5 cm$^{-1}$, 1105.37±5 cm$^{-1}$, 1013.09±5 cm$^{-1}$, 875.53±5 cm$^{-1}$, 865.08±5 cm$^{-1}$, 177.45±5 cm$^{-1}$, 568.10±5 cm$^{-1}$.

In another preferred embodiment, the infrared spectrum of the crystal form 1 is basically as shown in FIG. 4.

In another preferred embodiment, the polymorph is crystal form 2 of the maleate of the compound of formula (I), and the X-ray powder diffraction pattern of the crystal form 2 comprises diffraction angle 2θ (°) values selected from the following group: 5.02±0.2°, 5.36±0.2°, 14.04±0.2°, 20.96±0.2°, 21.42±0.2°, 23.00±0.2°.

In another preferred embodiment, the X-ray powder diffraction pattern of the crystal form 2 further comprises one or more (e.g. 2, 3, 4, 5, 6, 7, 8, 9, 10, 11, 12 or all) diffraction angle 2θ(°) values selected from the following group: 8.56±0.2°, 9.00±0.2°, 15.16±0.2°, 17.40±0.2°, 18.10±0.2°, 19.22±0.2°, 21.96±0.2°, 24.46±0.2°, 26.90±0.2°, 27.34±0.2°, 28.02±0.2°, 31.40±0.2°, 32.08±0.2°.

In another preferred embodiment, the X-ray powder diffraction pattern of the crystal form 2 further comprises diffraction angle 2θ (°) values selected from the following group: 8.56±0.2°, 9.00±0.2°, 17.40±0.2°, 19.22±0.2°, 24.46±0.2°, 27.34±0.2°, 28.02±0.2°, 32.08±0.2°.

In another preferred embodiment, the X-ray powder diffraction pattern of the crystal form 2 further comprises diffraction angle 2θ (°) values selected from the following group: 15.16±0.2°, 18.10±0.2°.

In another preferred embodiment, the X-ray powder diffraction pattern of the crystal form 2 further comprises one or more (for example, 2, 3, 4, 5, 6, 7, 8, 9, more or all) diffraction angle 2θ (°) values selected from table 3.

In another preferred embodiment, the X-ray powder diffraction pattern of the crystal form 2 is basically as shown in FIG. 5.

In another preferred embodiment, the differential scanning calorimetry analysis spectrum of the crystal form 2 has a characteristic peak at 159.25±5° C.

In another preferred embodiment, the differential scanning calorimetry analysis spectrum of the crystal form 2 has a characteristic peak at 159.25±2° C. (or 159.25±1° C.).

In another preferred embodiment, the differential scanning calorimetry analysis spectrum of the crystal form 2 is basically as shown in FIG. 6.

In another preferred embodiment, the thermogravimetric analysis spectrum of the crystal form 2 has characteristic peaks at 174.38±5° C. and 366.44±5° C.

In another preferred embodiment, the thermogravimetric analysis spectrum of the crystal form 2 has characteristic peaks at 174.38±2° C. and 366.44±2° C.

In another preferred embodiment, the infrared spectrum of the crystal form 2 has characteristic peaks at the following positions: 3382.52±5 cm$^{-1}$, 2960.69±5 cm$^{-1}$, 2850.44±5 cm$^{-1}$, 1647.70±5 cm$^{-1}$, 1560.25±5 cm$^{-1}$, 1474.41±5 cm$^{-1}$, 1354.95±5 cm$^{-1}$, 1202.41±5 cm$^{-1}$, 1178.29±5 cm$^{-1}$, 1106.85±5 cm$^{-1}$, 1012.71±5 cm$^{-1}$, 867.82±5 cm$^{-1}$, 712.49±5 cm$^{-1}$, 663.08±5 cm$^{-1}$, 570.85±5 cm$^{-1}$.

In another preferred embodiment, the thermogravimetric analysis spectrum of the crystal form 2 is basically as shown in FIG. 7.

In another preferred embodiment, the infrared spectrum of the crystal form 2 is basically as shown in FIG. 8.

In another preferred embodiment, the polymorph is crystal form 3 of the maleate of the compound of formula (I), and the X-ray powder diffraction pattern of the crystal form 3 comprises diffraction angle 2θ (°) values selected from the following group: 5.64±0.2°, 11.28±0.2°, 16.96±0.2°, 24.92±0.2°.

In another preferred embodiment, the X-ray powder diffraction pattern of the crystal form 3 further comprises one or more (for example, 2, 3, 4, 5, 6, 7, 8, 9, 10, 11, 12 or all) diffraction angle 2θ (°) values selected from the following group: 8.26±0.2°, 12.21±0.2°, 16.22±0.2°, 18.52±0.2°, 19.18±0.2°, 21.28±0.2°, 22.40±0.2°, 22.98±0.2°, 23.54±0.2°, 24.50±0.2°, 26.62±0.2°, 29.42±0.2°, 37.48±0.2°.

In another preferred embodiment, the X-ray powder diffraction pattern of the crystal form 3 further comprises diffraction angle 2θ (°) values selected from the following group: 19.18±0.2°, 26.62±0.2°, 29.42±0.2°.

In another preferred embodiment, the X-ray powder diffraction pattern of the crystal form 3 further comprises diffraction angle 2θ (°) values selected from the following group: 8.26±0.2°, 16.22±0.2°, 18.52±0.2°, 23.54±0.2°, 24.50±0.2°.

In another preferred embodiment, the X-ray powder diffraction pattern of the crystal form 3 comprises one or more (for example, 2, 3, 4, 5, 6, 7, 8, 9, more or all) diffraction angle 2θ (°) values selected from table 4.

In another preferred embodiment, the X-ray powder diffraction pattern of the crystal form 3 is basically as shown in FIG. 9.

In another preferred embodiment, the differential scanning calorimetry analysis spectrum of the crystal form 3 has a characteristic peak at 114.72±5° C.

In another preferred embodiment, the differential scanning calorimetry analysis spectrum of the crystal form 3 has a characteristic peak at 114.72±2° C. (or 114.72±1° C.).

In another preferred embodiment, the differential scanning calorimetry analysis spectrum of the crystal form 3 is basically as shown in FIG. 10.

In another preferred embodiment, the polymorph is crystal form 4 of the maleate of the compound of formula (I), and the X-ray powder diffraction pattern of the crystal form 4 comprises diffraction angle 2θ (°) values selected from the following group: 5.08±0.2°, 5.62±0.2°, 13.98±0.2°, 22.72±0.2°.

In another preferred embodiment, the X-ray powder diffraction pattern of the crystal form 4 further comprises one or more (for example, 2, 3, 4, 5, 6, 7, 8, 9, 10, 11, 12, 13, 14 or all) diffraction angle 2θ(°) values selected from the following group: 8.54±0.2°, 11.32±0.2°, 15.78±0.2°, 17.08±0.2°, 18.10±0.2°, 20.66±0.2°, 21.56±0.2°, 23.50±0.2°, 25.76±0.2°, 27.08±0.2°, 28.02±0.2°, 28.45±0.2°, 28.55±0.2°, 32.16±0.2°, 34.48±0.2°.

In another preferred embodiment, the X-ray powder diffraction pattern of the crystal form 4 further diffraction angle 2θ (°) values selected from the following group: 8.54±0.2°, 11.32±0.2°, 17.08±0.2°, 18.10±0.2°, 20.66±0.2°, 25.76±0.2°.

In another preferred embodiment, the X-ray powder diffraction pattern of the crystal form 4 comprises one or more (for example, 2, 3, 4, 5, 6, 7, 8, 9, more or all) diffraction angle 2θ (°) values selected from table 5.

In another preferred embodiment, the X-ray powder diffraction pattern of the crystal form 4 is basically as shown in FIG. 11.

In another preferred embodiment, the differential scanning calorimetry analysis spectrum of the crystal form 4 has a characteristic peak at 175.74±5° C.

In another preferred embodiment, the differential scanning calorimetry analysis spectrum of the crystal form 4 has a characteristic peak at 175.74±2° C. (or 175.74±1° C.).

In another preferred embodiment, the differential scanning calorimetry analysis spectrum of the crystal form 4 is basically as shown in FIG. 12.

In another preferred embodiment, the polymorph is crystal form I of the maleate of the compound of formula (I), and the X-ray powder diffraction pattern of the crystal form I comprises diffraction angle 2θ (°) values selected from the following group: 5.00±0.2°, 5.40±0.2°, 14.23±0.2°, 22.40±0.2°, 23.28±0.2°.

In another preferred embodiment, the X-ray powder diffraction pattern of the crystal form I further comprises diffraction angle 2θ (°) values selected from the following group: 8.64±0.2°, 9.80±0.2°, 15.04±0.2°, 16.60±0.2°, 17.40±0.2°, 18.13±0.2°, 19.64±0.2°, 20.41±0.2°, 24.72±0.2°, 27.09±0.2°, 28.40±0.2°.

In another preferred embodiment, the X-ray powder diffraction pattern of the crystal form I further comprises diffraction angle 2θ (°) values selected from the following group: 11.16±0.2°, 31.00±0.2°.

In another preferred embodiment, the X-ray powder diffraction pattern of the crystal form I comprises one or more (e.g. 2, 3, 4, 5, 6, 7, 8, 9, more or all) diffraction angle 2θ (°) values selected from table 1.

In another preferred embodiment, the X-ray powder diffraction pattern of the crystal form I is basically as shown in FIG. 17.

In another preferred embodiment, the differential scanning calorimetry analysis spectrum of the crystal form I has a characteristic peak at 159.91±5° C.

In another preferred embodiment, the differential scanning calorimetry analysis spectrum of the crystal form I has a characteristic peak at 159.91±2° C. (or 159.91±1° C.).

In another preferred embodiment, the differential scanning calorimetry analysis spectrum of the crystal form I is basically as shown in FIG. 18.

In another preferred embodiment, in the fumarate of the compound of formula (I), the molar ratio of the compound of formula (I) to fumaric acid is 2:1.

In another preferred embodiment, the polymorph is crystal form A of the fumarate of the compound of formula (I), and the X-ray powder diffraction pattern of the crystal form A comprises diffraction angle 2θ (°) values selected from the following group: 14.24±0.2°, 19.44±0.2°, 21.24±0.2°, 23.77±0.2°, 24.57±0.2°.

In another preferred embodiment, the X-ray powder diffraction pattern of the crystal form A further comprises one or more (for example, 2, 3, 4, 5, 6, 7, 8, 9, 10, 11, 12, 13, 14, 15, 16, 17, 18, 19, 20, 21, 22, 23, 24, 25, 26 or all) diffraction angle 2θ(°) values selected from the following group: 10.60±0.2°, 12.95±0.2°, 14.72±0.2°, 15.88±0.2°, 16.79±0.2°, 17.93±0.2°, 18.41±0.2°, 18.93±0.2°, 20.67±0.2°, 22.16±0.2°, 22.80±0.2°, 24.88±0.2°, 25.32±0.2°, 26.13±0.2°, 27.24±0.2°, 27.64±0.2°, 28.15±0.2°, 28.64±0.2°, 29.33±0.2°, 29.64±0.2°, 32.08±0.2°, 32.73±0.2°, 33.36±0.2°, 35.36±0.2°, 35.96±0.2°, 38.28±0.2°, 38.64±0.2°.

In another preferred embodiment, the X-ray powder diffraction pattern of the crystal form A further comprises diffraction angle 2θ (°) values selected from the following group: 10.60±0.2°, 12.95±0.2°, 15.88±0.2°, 16.79±0.2°, 17.93±0.2°, 18.41±0.2°, 20.67±0.2°, 22.80±0.2°, 29.64±0.2°, 33.36±0.2°.

In another preferred embodiment, the X-ray powder diffraction pattern of the crystal form A further comprises diffraction angle 2θ (°) values selected from the following group: 14.72±0.2°, 22.16±0.2°, 24.88±0.2°, 28.15±0.2°, 28.64±0.2°, 29.33±0.2°, 32.08±0.2°, 35.36±0.2°.

In another preferred embodiment, the X-ray powder diffraction pattern of the crystal form A comprises one or more (for example, 2, 3, 4, 5, 6, 7, 8, 9, more or all) diffraction angle 2θ (°) values selected from table 6.

In another preferred embodiment, the X-ray powder diffraction pattern of the crystal form A is basically as shown in FIG. 13.

In another preferred embodiment, the differential scanning calorimetry analysis spectrum of the crystal form A has a characteristic peak at 218.67±5° C.

In another preferred embodiment, the differential scanning calorimetry analysis spectrum of the crystal form A has a characteristic peak at 218.67±2° C. (or 218.67±1° C.).

In another preferred embodiment, the differential scanning calorimetry analysis spectrum of the crystal form A is basically as shown in FIG. 14.

In the second aspect, the present invention provides a pharmaceutical composition comprising the pharmaceutically acceptable salt of the compound of formula (I) or the polymorph thereof described in the first aspect and a pharmaceutically acceptable carrier.

In the third aspect, the present invention provides a use of the pharmaceutically acceptable salt of the compound of formula (I) or the polymorph thereof described in the first aspect or the pharmaceutical composition described in the second aspect for the preparation of medcine for the prevention or treatment of CDK9-related diseases.

In another preferred embodiment, the CDK9-related diseases are cancers.

In another preferred embodiment, the cancers are one or more cancers selected from the following group: non-small cell lung cancer, small cell lung cancer, lung adenocarcinoma, lung squamous cell carcinoma, pancreatic cancer, prostate cancer, bladder cancer, liver cancer, skin cancer, glioma, breast cancer, melanoma, malignant glioma, rhabdomyosarcoma, ovarian cancer, astrocytoma, Ewing's sarcoma, retinoblastoma, epithelial cell carcinoma, colon cancer, kidney cancer, stomach intestinal stromal tumor, leukemia, histocytic lymphoma, and nasopharyngeal carcinoma.

In the fourth aspect, the present invention provides a preparation method for the pharmaceutically acceptable salt of the compound of formula (I) or the polymorph thereof described in the first aspect, wherein the polymorph is the crystal form I of the maleate of the compound of formula (I) and the method comprises the step:

(1) the compound of formula (I) and maleic acid are stirred in an organic solvent to form the crystal form I of the maleate of the compound of formula (I); wherein the molar ratio of the compound of formula (I) to the maleic acid is 1:2.

In another preferred embodiment, in step (1), the stirred means that: firstly stirred at 50-85° C. (preferably 70-85° C. or 75-80° C.) (for example, for 1-4 hours or 1-2 hours); then the mixed system is cooled to 0-35° C. (preferably 10-25° C.) and further stirred (for example, 1-4 hours or 2-3 hours).

In another preferred embodiment, in step (1), the organic solvent is acetonitrile, ethanol, or a combination thereof.

In another preferred embodiment, step (1) comprises the steps:
(1-1) the compound of formula (I) is dissolved in an organic solvent to obtain a solution 1 of the compound of formula (I);
(1-2) maleic acid is dissolved in an organic solvent to obtain a solution 2 of maleic acid;
(1-3) the solution 1 of the compound of formula (I) is added dropwise to the solution 2 of maleic acid at 50-85° C. (preferably 70-85° C. or 75-80° C.) and stirred (for example, 1-4 hours or 1-2 hours); then the mixed system is cooled to 0-35° C. (preferably 10-25° C.), further stirred (for example, 1-4 hours or 2-3 hours), and filtered, and the solid is collected to obtain the crystal form I of the maleate of the compound of formula (I).

In another preferred embodiment, in step (1), the molar ratio of the compound of formula (I) to maleic acid is 1:(1.5-3).

In another preferred embodiment, in step (1), the molar ratio of the compound of formula (I) to maleic acid is 1:(2-3), preferably 1:(2.1-2.2).

In another preferred embodiment, in step (1-3), the solid collected after filtration is rinsed with acetonitrile and dried to obtain the crystal form I of the maleate of the compound of formula (I).

In the fifth aspect, the present invention provides a preparation method for the pharmaceutically acceptable salt of the compound of formula (I) or the polymorph thereof described in the first aspect, wherein the polymorph is the crystal form 1 of the maleate of the compound of formula (I) and the method comprises the steps:
(1) the compound of formula (I) and maleic acid are stirred in an organic solvent to form the maleate of the compound of formula (I); wherein the molar ratio of the compound of formula (I) to the maleic acid is 1:2;
(2a) the maleate of the compound of formula (I) obtained in step (1) is dissolved in the first crystallization solvent to obtain a solution containing the maleate of the compound of formula (I);
(3a) the solution obtained in step (2a) is crystallized, and filtered after the crystallization, and the solid is collected to obtain the crystal form 1 of the maleate of the compound of formula (I).

In another preferred embodiment, step (3a) is: the solution obtained in step (2a) is crystallized at 0-25° C., and filtered after the crystallization, and the solid is collected, thereby obtaining the crystal form 1 of the maleate of the compound of formula (I).

In another preferred embodiment, step (3a) is: the solution obtained in step (2a) is crystallized at 70-80° C. (preferably 75° C.); after crystallization, the mixture is cooled and filtered, and the solid is collected to obtain the crystal form 1 of the maleate of the compound of formula (I).

In another preferred embodiment, step (3a) is: the solution obtained in step (2a) is crystallized at 70-80° C. (preferably 75° C.); after crystallization, the mixture is cooled to 0-30° C. (preferably 0-15° C. or 2-10° C.) and filtered, and the solid is collected to obtain the crystal form 1 of the maleate of the compound of formula (I).

In another preferred embodiment, in step (3a), the solid collected after filtration is dried at 55-65° C. (preferably 60° C.) to obtain the crystal form 1 of the maleate of the compound of formula (I).

In another preferred embodiment, in step (3a), the solid collected after filtration can also be recrystallized once or twice to obtain the crystal form 1. Optionally, the seed crystals of crystal form 1 can be added during the recrystallization process.

In another preferred embodiment, the maleate of the compound of formula (I) obtained in step (1) is the crystal form I of the maleate of the compound of formula (I) obtained in step (1).

In another preferred embodiment, in step (1), the stirred means that: firstly stirred at 50-85° C. (preferably 70-85° C. or 75-80° C.) (for example, for 1-4 hours or 1-2 hours); then the mixed system is cooled to 0-35° C. (preferably 10-25° C.) and further stirred (for example, for 1-4 hours or 2-3 hours).

In another preferred embodiment, in step (1), the organic solvent is acetonitrile, ethanol, or a combination thereof.

In another preferred embodiment, the first crystallization solvent is acetonitrile or a mixed solvent of acetonitrile and water.

In another preferred embodiment, the first crystallization solvent is a mixed solvent of acetonitrile and water.

In another preferred embodiment, the first crystallization solvent is a mixed solvent of acetonitrile and water; wherein the volume ratio of acetonitrile and water is 50:1 to 1:1 (preferably 50:1 to 10:1); preferably, 40:1 to 1:1 (preferably 40:1 to 10:1); more preferably, 30:1 to 1:1 (preferably 30:1 to 10:1) or 25:1 to 1:1 (preferably 25:1 to 4:1 or 25:1 to 15:1).

In another preferred embodiment, step (2a) comprises the step: under the protection of nitrogen, the maleate of the compound of formula (I) is mixed with the first crystallization solvent and then dissolved at refluxing temperature to obtain a solution containing the maleate of the compound of formula (I).

In another preferred embodiment, step (3a) is performed under nitrogen protection.

In another preferred embodiment, step (1) comprises the steps:
(1-1) the compound of formula (I) is dissolved in an organic solvent to obtain a solution 1 of the compound of formula (I);
(1-2) maleic acid is dissolved in an organic solvent to obtain a maleic acid solution 2;
(1-3) firstly, the solution 1 of the compound of formula (I) is added dropwise to the maleic acid solution 2 at 50-85° C. (preferably 70-85° C. or 75-80° C.) and stirred (for example, for 1-4 hours or 1-2 hours); then the mixed system is cooled to 0-35° C. (preferably 10-25° C.), further stirred (for example, for 1-4 hours or 2-3 hours) and then filtered, and the solid is collected to obtain the crystal form I of the maleate of the compound of formula (I).

In another preferred embodiment, in step (1), the molar ratio of the compound of formula (I) to the maleic acid is 1:(1.5-3).

In another preferred embodiment, in step (1), the molar ratio of the compound of formula (I) to the maleic acid is 1:(2-3), preferably 1:(2.1-2.2).

In another preferred embodiment, in step (1-3), the solid collected after filtration is rinsed with acetonitrile and dried to obtain the crystal form I of the maleate of the compound of formula (I).

In the sixth aspect, the present invention provides a preparation method for the pharmaceutically acceptable salt of the compound of formula (I) or the polymorph thereof described in the first aspect, wherein the polymorph is crystal form 2 of the maleate of the compound of formula (I) and the method comprises the steps:
- (1) the compound of formula (I) and maleic acid are stirred in an organic solvent to form the maleate of the compound of formula (I); wherein the molar ratio of the compound of formula (I) to the maleic acid is 1:2;
- (2b) the maleate of the compound of formula (I) obtained in step (1) is stirred in a second crystallization solvent at 0-50° C. (preferably 10-30 or 20-25° C.) (for example, for 6-36 hours or 8-24 hours) and then filtered, and the solid is collected to obtain the crystal form 2 of the maleate of the compound of formula (I).

In another preferred embodiment, in step (2b), the solid collected after filtration is dried at 35-55° C. (preferably 40-50° C.) to obtain the crystal form 2 of the maleate of the compound of formula (I).

In another preferred embodiment, the maleate of the compound of formula (I) obtained in step (1) is the crystal form I of the maleate of the compound of formula (I) obtained in step (1).

In another preferred embodiment, in step (1), the stirred means that: firstly stirred at 50-85° C. (preferably 70-85° C. or 75-80° C.) (for example, for 1-4 hours or 1-2 hours); then the mixed system is cooled to 0-35° C. (preferably 10-25° C.) and further stirred (for example, for 1-4 hours or 2-3 hours).

In another preferred embodiment, in step (1), the organic solvent is acetonitrile, ethanol, or a combination thereof.

In another preferred embodiment, the second crystallization solvent is methyl tert-butyl ether, ethyl acetate or a combination thereof.

In another preferred embodiment, step (1) comprises the steps:
- (1-1) the compound of formula (I) is dissolved in an organic solvent to obtain a solution 1 of the compound of formula (I);
- (1-2) maleic acid is dissolved in an organic solvent to obtain a maleic acid solution 2;
- (1-3) firstly, the solution 1 of the compound of formula (I) is added dropwise to the maleic acid solution 2 at 50-85° C. (preferably 70-85° C. or 75-80° C.) and stirred (for example, for 1-4 hours or 1-2 hours); then the mixed system is cooled to 0-35° C. (preferably 10-25° C.), further stirred (for example, for 1-4 hours or 2-3 hours) and then filtered, and the solid is collected to obtain the crystal form I of the maleate of the compound of formula (I).

In another preferred embodiment, in step (1), the molar ratio of the compound of formula (I) to maleic acid is 1:(1.5-3).

In another preferred embodiment, in step (1), the molar ratio of the compound of formula (I) to maleic acid is 1:(2-3), preferably 1:(2.1-2.2).

In another preferred embodiment, in step (1-3), the solid collected after filtration is rinsed with acetonitrile and dried to obtain the crystal form I of the maleate of the compound of formula (I).

In the seventh aspect, the present invention provides a preparation method for the pharmaceutically acceptable salt of the compound of formula (I) or the polymorph thereof described in the first aspect, wherein the polymorph is crystal form 3 of the maleate of the compound of formula (I) and the method comprises the steps:
- (1) the compound of formula (I) and maleic acid are stirred in an organic solvent to form the maleate of the compound of formula (I); wherein the molar ratio of the compound of formula (I) to the maleic acid is 1:2;
- (2c) the maleate of the compound of formula (I) obtained in step (1) is stirred in a third crystallization solvent at 45-55° C. (preferably 50° C.) (for example, for 6-48 hours or 12-36 hours) and then filtered, and the solid is collected to obtain the crystal form 3 of the maleate of the compound of formula (I).

In another preferred embodiment, in step (2c), the solid collected after filtration is dried to obtain the crystal form 3 of the maleate of the compound of formula (I).

In another preferred embodiment, the maleate of the compound of formula (I) obtained in step (1) is the crystal form I of the maleate of the compound of formula (I) obtained in step (1).

In another preferred embodiment, in step (1), the stirred means that: firstly stirred at 50-85° C. (preferably 70-85° C. or 75-80° C.) (for example, for 1-4 hours or 1-2 hours); then the mixed system is cooled to 0-35° C. (preferably 10-25° C.) and further stirred (for example, for 1-4 hours or 2-3 hours).

In another preferred embodiment, in step (1), the organic solvent is acetonitrile, ethanol, or a combination thereof.

In another preferred embodiment, the third crystallization solvent is a mixed solvent of acetone and water.

In another preferred embodiment, the third crystallization solvent is a mixed solvent of acetone and water; wherein the volume ratio of acetone and water is 20:1 to 5:1; preferably, 15:1 to 10:1.

In another preferred embodiment, step (1) comprises the steps:
- (1-1) the compound of formula (I) is dissolved in an organic solvent to obtain a solution 1 of the compound of formula (I);
- (1-2) maleic acid is dissolved in an organic solvent to obtain a maleic acid solution 2;
- (1-3) firstly, the solution 1 of the compound of formula (I) is added dropwise to the maleic acid solution 2 at 50-85° C. (preferably 70-85° C. or 75-80° C.) and stirred (for example, for 1-4 hours or 1-2 hours); then the mixed system is cooled to 0-35° C. (preferably 10-25° C.), further stirred (for example, for 1-4 hours or 2-3 hours) and then filtered, and the solid is collected to obtain the crystal form I of the maleate of the compound of formula (I).

In another preferred embodiment, in step (1), the molar ratio of the compound of formula (I) to maleic acid is 1:(1.5-3).

In another preferred embodiment, in step (1), the molar ratio of the compound of formula (I) to maleic acid is 1:(2-3), preferably 1:(2.1-2.2).

In another preferred embodiment, in step (1-3), the solid collected after filtration is rinsed with acetonitrile and dried to obtain the crystal form I of the maleate of the compound of formula (I).

In the eighth aspect, the present invention provides a preparation method for the pharmaceutically acceptable salt of the compound of formula (I) or the polymorph thereof described in the first aspect, wherein the polymorph is crystal form 4 of the maleate of the compound of formula (I) and the method comprises the steps:
- (1) the compound of formula (I) and maleic acid are stirred in an organic solvent to form the maleate of the compound of formula (I); wherein the molar ratio of the compound of formula (I) to the maleic acid is 1:2;

(2d) the maleate of the compound of formula (I) obtained in step (1) is stirred in a fourth crystallization solvent at 20-60° C. (preferably 25-50° C.) (for example, for 6-48 hours or 12-36 hours) and then filtered, and the solid is collected to obtain the crystal form 4 of the maleate of the compound of formula (I).

In another preferred embodiment, in step (2d), the solid collected after filtration is dried to obtain the crystal form 4 of the maleate of the compound of formula (I).

In another preferred embodiment, the maleate of the compound of formula (I) obtained in step (1) is the crystal form I of the maleate of the compound of formula (I) obtained in step (1).

In another preferred embodiment, in step (1), the stirred means that: firstly stirred at 50-85° C. (preferably 70-85° C. or 75-80° C.) (for example, for 1-4 hours or 1-2 hours); then the mixed system is cooled to 0-35° C. (preferably 10-25° C.) and further stirred (for example, for 1-4 hours or 2-3 hours).

In another preferred embodiment, in step (1), the organic solvent is acetonitrile, ethanol, or a combination thereof.

In another preferred embodiment, the fourth crystallization solvent is ethanol, isopropanol, a mixed solvent of ethanol and water, or a mixed solvent of isopropanol and water.

In another preferred embodiment, the fourth crystallization solvent is a mixed solvent of ethanol and water; wherein the volume ratio of ethanol and water is 20:1 to 5:1; preferably, 15:1 to 10:1.

In another preferred embodiment, the fourth crystallization solvent is a mixed solvent of isopropanol and water; wherein the volume ratio of isopropanol to water is 20:1 to 5:1; preferably, 15:1 to 10:1.

In another preferred embodiment, step (1) comprises the steps:

(1-1) the compound of formula (I) is dissolved in an organic solvent to obtain a solution 1 of the compound of formula (I);

(1-2) maleic acid is dissolved in an organic solvent to obtain a maleic acid solution 2;

(1-3) firstly, the solution 1 of the compound of formula (I) is added dropwise to the maleic acid solution 2 at 50-85° C. (preferably 70-85° C. or 75-80° C.) and stirred (for example, for 1-4 hours or 1-2 hours); then the mixed system is cooled to 0-35° C. (preferably 10-25° C.), further stirred (for example, for 1-4 hours or 2-3 hours) and then filtered, and the solid is collected to obtain the crystal form I of the maleate of the compound of formula (I).

In another preferred embodiment, in step (1), the molar ratio of the compound of formula (I) to maleic acid is 1:(1.5-3).

In another preferred embodiment, in step (1), the molar ratio of the compound of formula (I) to maleic acid is 1:(2-3), preferably 1:(2.1-2.2).

In another preferred embodiment, in step (1-3), the solid collected after filtration is rinsed with acetonitrile and dried to obtain the crystal form I of the maleate of the compound of formula (I).

In the ninth aspect, the present invention provides a preparation method for the pharmaceutically acceptable salt of the compound of formula (I) or the polymorph thereof described in the first aspect, wherein the polymorph is crystal form A of the fumarate of the compound of formula (I) and the method comprises the steps:

(a) the compound of formula (I) and fumaric acid are stirred in an organic solvent at 40-60° C. (preferably 45-55° C.) (for example, for 0.1-2 hours or 0.5-1 hours);

(b) then the mixed system is cooled to 10-30° C. (preferably 20-25° C.) and further stirred (for example, for 0.5-3 hours or 1-2 hours), and then filtered, and the solid is collected to obtain the crystal form A of the fumarate of the compound of formula (I).

In another preferred embodiment, the method comprises the steps:

(i) the compound of formula (I) is dissolved in an organic solvent (such as acetonitrile) to obtain a solution 1' of the compound of formula (I);

(ii) fumaric acid is dissolved in an organic solvent (e.g. ethanol) to obtain a fumaric acid solution 2';

(iii) the solution 1' of the compound of formula (I) is added dropwise to the fumaric acid solution 2' at 40-60° C. (preferably 45-55° C.) and stirred (for example, for 1-4 hours or 1-2 hours), then, the mixed system is cooled to 10-30° C. (preferably 20-25° C.) and further stirred (for example, for 1-4 hours or 2-3 hours) and filtered, and the solid is collected to obtain the crystal form A of the fumarate of the compound of formula (I).

In another preferred embodiment, in each step, the organic solvent is independently acetonitrile, ethanol, or a combination thereof.

In another preferred embodiment, the molar ratio of the compound of formula (I) to the fumaric acid is 1:(0.5-0.7), preferably 1:(0.5-0.6).

In another preferred embodiment, the solid collected after filtration is rinsed with acetonitrile and dried (for example, at 45-55° C. or 50° C.) to obtain the crystal form A of the fumarate of the compound of formula (I).

The main advantages of the present invention include:

After long-term and in-depth research, the inventors unexpectedly discovered from many kinds of salts that the maleate or fumarate of the compound of formula (I) has good physical and chemical properties. Accordingly, the present invention provides multiple polymorphs of the maleate or fumarate of the compound of formula (I), which are respectively the crystal form I, crystal form 1, crystal form 2, crystal form 3, crystal form 4 of the maleate of the compound of formula (I) and the crystal form A of the fumarate of the compound of formula (I). The polymorphs of the present invention have good stability, good solubility, and are not easy to absorb moisture, and solve the defects of the free base, such as poor solubility, strong hygroscopicity, and poor stability. At the same time, the polymorphs of the present invention maintain good inhibition to CDK9, thereby can be further developed into medicine for prevention and treatment of CDK9-related diseases.

It should be understood that, within the scope of the present invention, the above-mentioned technical features of the present invention and the technical features specifically described in the following (such as the embodiments) can be combined with each other to form a new or preferred technical solution. Due to space limitations, it is not repeated here.

EMBODIMENTS

Figure 1:
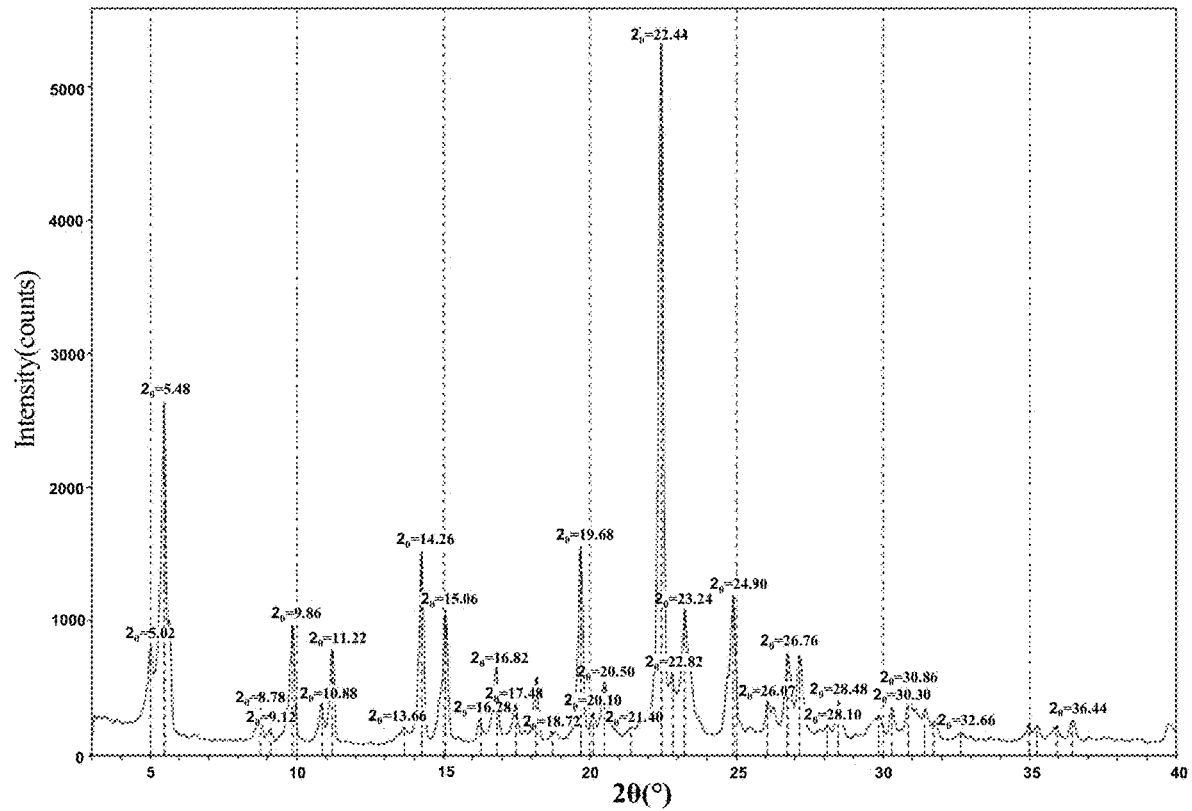
FIG. 1 is an XRPD pattern of the crystal form 1 of the maleate of the compound of formula (I) prepared in Example 2.

Compound of formula (I) of the present invention

The compound of formula (I) of the present invention is shown as the following formula:

The name of the compound is 4-(((4-(5-chloro-2-(((1R,4r)-4-(((R)-1-methoxypropyl-2-yl) amino)cyclohexyl)amino)pyridin-4-yl)thiazol-2-yl)amino)methyl)tetrahydro-2H-pyran-4-carbon itrile, which can also be 4-[[[4-[5-chloro-2-[[trans-4-[[(1R)-2-methoxy-1-methylethyl]amino]cyclohexyl]amino]-4-pyridyl]-2-thiazolyl]amino]methyl]-tetrahydro-2H-pyran-4-cyano. The specific preparation method of the compound can refer to the preparation method of Example 1 in CN108727363A, and the compound can be used to inhibit the activity of cyclin-dependent kinases (CDK) and cyclins, especially the activity of CDK9.

In the present invention, "compound of formula (I)" and "the free base of compound of formula (I)" can be used interchangeably.

Polymorphs of the Present Invention

Solids exist either in amorphous form or in crystal form. In the case of a crystal form, the molecules are positioned within three-dimensional lattice sites. When a compound crystallizes from a solution or slurry, it can crystallize in different spatial lattice arrangements (this property is called "polymorphism") to form crystals with different crystal forms. These various crystal forms are known as "polymorphs". Different polymorphs of a given substance may differ from each other in one or more physical properties (such as solubility and dissolution rate, true specific gravity, crystal shape, packing method, fluidity, and/or solid state stability).

The "crystallization" can be achieved by manipulating the solution so that the solubility limit of the compound of interest is exceeded, thereby completing production-scale crystallization. This can be done in a variety of ways, for example, dissolving the compound at a relatively high temperature, and then cooling the solution below the saturation limit, or reducing the liquid volume by boiling, atmospheric evaporation, vacuum drying, or some other method. Alternatively, the solubility of the compound of interest can be reduced by adding an antisolvent or a solvent in which the compound has low solubility, or a mixture of such solvents. Another alternative is to adjust the pH to reduce solubility. A detailed description of crystallization can be referred from Crystallization, Third Edition, J W Mullens, Butterworth-Heineman Ltd., 1993, ISBN 0750611294.

The "crystallization" can be achieved by mixing the compound of formula (I) with a corresponding acid or a solution of the corresponding acid in a suitable solvent to form a turbid liquid, or mixing the compound of formula (I) with a suitable solvent to form a turbid liquid, and then stirring to obtain crystal forms. Suitable solvents can be water or organic solvents.

The "crystallization" can be achieved by placing a solution of the compound of formula (I) or a solution containing the compound of formula (I) and corresponding acid at a certain temperature and slowly evaporating the solvent to obtain crystal forms.

The "adding an antisolvent" or "adding an anti-solvent" in the present invention refers to a method to obtain crystal froms by adding another suitable solvent to a solution of the compound of formula (I).

If salt formation and crystallization are desired to occur at the same time, if the salt is less soluble in the reaction medium than the raw material, then the addition of an appropriate acid or base can lead to direct crystallization of the desired salt. Similarly, in a medium with less solubility in the final desired form than the reactants, the final product will directly crystallize at the time of the completion of the synthesis reaction.

The optimization of crystallization may include seeding the crystallization medium with crystals of the desired form as seeds. In addition, many crystallization methods use a combination of the above strategies. One example is to dissolve the compound of interest in a solvent at a high temperature, and then add an appropriate volume of antisolvent in a controlled manner to make the system just below the saturation level. At this time, a seed crystal of a desired form can be added (and the integrity of the seed crystal is maintained), and then the system is cooled to complete the crystallization.

As used herein, "the crystal of the present invention", "the crystal form of the present invention", "the polymorph of the present invention" and the like can be used interchangeably.

As used herein, the term "the polymorph of the present invention" comprises the polymorphs of the compound of formula (I) or a pharmaceutically acceptable salt (such as maleate, fumarate), and also comprises different polymorphs of the same salt.

Preferably, the polymorphs of the present invention include (but are not limited to): crystal form I, crystal form 1, crystal form 2, crystal form 3, or crystal form 4 of the maleate of the compound of formula (I), and crystal form A of the fumarate of the compound of formula (I).

In the present invention, certain crystal forms can be converted into each other, so the present invention also provides a method for conversion of crystal forms into each other.

Identification and Properties of Polymorphs

In the present invention, after preparing the polymorph of the compound of formula (I), its properties are studied by the following methods and instruments, for example, X-ray powder diffraction (XRPD), differential calorimetric scanning analysis (DSC), TGA, IR, etc.

X-ray powder diffraction: the method for determining the X-ray powder diffraction of the crystal form was known in the art. For example, an X-ray powder diffractometer is used to acquire the spectrum with a copper radiation target at a scanning rate of 2° per minute.

The polymorph of the salt of the compound of formula (I) of the present invention has a specific crystal form and has specific characteristic peaks in an X-ray powder diffraction (XRPD) pattern.

Differential scanning calorimetry, also known as "differential calorimetric scanning analysis" (DSC), is a technique that measures the relationship between the energy difference and the temperature in the measured substance or the reference substance during a heating process.

The peak position, shape and number of peaks on the DSC spectrum are related to the nature of the substance, so it can be used to identify the substance qualitatively. This method is commonly used in the art to detect the phase transition temperature, glass transition temperature, reaction heat and other parameters of substances.

Pharmaceutical Composition and its Uses

The active ingredient of the present invention is the polymorph of the present invention, for example, the maleate of the compound of formula (I) or its polymorph or the fumarate of the compound of formula (I) or its polymorph.

The active ingredient of the present invention can be used to inhibit the activity of cyclin-dependent kinases (CDK) and cyclins, especially the activity of CDK9. Therefore, the active ingredient of the present invention and the pharmaceutical composition containing the active ingredient of the present invention can be used to treat or prevent CDK9-related diseases, such as cancer, including (but not limited to) one or more diseases selected from the following group: non-small cells lung cancer, small cell lung cancer, lung adenocarcinoma, lung squamous cell carcinoma, pancreatic cancer, prostate cancer, bladder cancer, liver cancer, skin cancer, glioma, breast cancer, melanoma, malignant glioma, rhabdomyosarcoma, ovarian cancer, astrocytoma, Ewing's sarcoma, retinoblastoma, epithelial cell carcinoma, colon cancer, kidney cancer, gastrointestinal stromal tumor, leukemia, histocytic lymphoma, and nasopharyngeal carcinoma.

The pharmaceutical composition of the present invention comprises the active ingredient of the present invention and a pharmaceutically acceptable carrier. The pharmaceutical composition of the present invention may also contain other optional therapeutic agents.

As used herein, "pharmaceutically acceptable carrier" refers to a non-toxic, inert, solid, semi-solid substance or liquid filler, diluent, packaging material or auxiliary preparation or any type of excipient, which is compatible with patient, preferably a mammal, more preferably a human, and suitable for delivering the active agent to the target without terminating the activity of the agent.

In the course of treatment, the drug of the present invention can be used alone or in combination with one or more other therapeutic agents according to the situation. The combined use may be the simultaneous administration of one or more other therapeutic agents with the use of the drug of the present invention, or the administration of one or more other therapeutic agents before or after the use of the drug of the present invention.

Generally, the active ingredient of the present invention can be administered in a suitable dosage form with one or more pharmaceutical carriers. These dosage forms are suitable for oral, rectal, topical, intraoral, and other parenteral administration (for example, subcutaneous, intramuscular, intravenous, etc.). The above-mentioned dosage forms can be prepared from the active ingredient of the present invention and one or more carriers or excipients through general pharmaceutical methods. The above-mentioned carrier needs to be compatible with the active ingredient or other auxiliary materials of the present invention. For solid preparations, commonly used non-toxic carriers include but are not limited to mannitol, lactose, starch, magnesium stearate, cellulose, glucose, sucrose and the like. Carriers for liquid preparations include water (preferably sterile water for injection), physiological saline, aqueous glucose solution, ethylene glycol, polyethylene glycol, and the like. The active ingredient of the present invention can form a solution or a suspension with the above-mentioned carrier.

The pharmaceutical composition of the present invention is formulated, quantified and administered in a manner conforming to medical practice standards. The "therapeutically effective amount" of the active ingredient of the present invention is determined by factors such as the specific condition to be treated, the individual to be treated, the cause of the condition, the target of the drug, and the mode of administration.

As used herein, "therapeutically effective amount" refers to an amount that can produce function or activity on patients (eg, humans and/or animals) and can be accepted by humans and/or animals.

The therapeutically effective amount of the pharmaceutical composition of the present invention or the active ingredient contained in the pharmaceutical composition is preferably 0.1 mg-5 g/kg (per body weight). Generally, as far as the dosage used for an adult treatment is concerned, the administered dosage is usually in the range of 0.02-5000 mg/day, for example, about 1-1500 mg/day. The dose may be one dose, or a dose in the simultaneous administration, or divided doses at appropriate intervals, for example, two, three, four or more divided doses per day. Those skilled in the art can understand that although the above-mentioned dosage range can be given, the specific effective amount can be appropriately adjusted according to the patient's condition and in conjunction with the doctor's diagnosis.

As used herein, "patient" refers to an animal, preferably a mammal, more preferably a human. The term "mammal" refers to warm-blooded spinal mammals, including cats, dogs, rabbits, bears, foxes, wolves, monkeys, deer, rats, pigs, and humans.

As used herein, "treating" refers to reducing, delaying progression, attenuating, preventing or maintaining an existing disease or condition (e.g. cancer). "Treatment" also comprises curing one or more symptoms of a disease or condition, preventing its development or alleviating to a certain degree.

The active ingredient of the present invention can be prepared by a variety of synthetic methods well known to those skilled in the art, including the specific embodiments listed below, the embodiments formed by combining them with other chemical synthesis methods, and the equivalent alternatives well known to those skilled in the art. Preferred implementations include but are not limited to the embodiments of the present invention.

The present invention will be further illustrated below in conjunction with specific embodiments. It should be understood that these embodiments are only used to illustrate the present invention and not to limit the scope of the present invention. The experimental methods without indication of specific conditions in the following examples usually follow the conventional conditions or the conditions recommended by the manufacturer. Unless otherwise stated, percentages and parts are calculated by weight.

Unless otherwise defined, the terms used herein have the same meaning as those familiar to those skilled in the art.

Unless otherwise defined, any reagents or instruments used herein are commercially available.

Any method and material similar or equivalent to the content described herein can be used in the present invention.

As used herein, the term "room temperature" generally refers to 4-30° C., preferably 25±5° C.

Abbreviations: ACN Stands for Acetonitrile.

Figure 19:
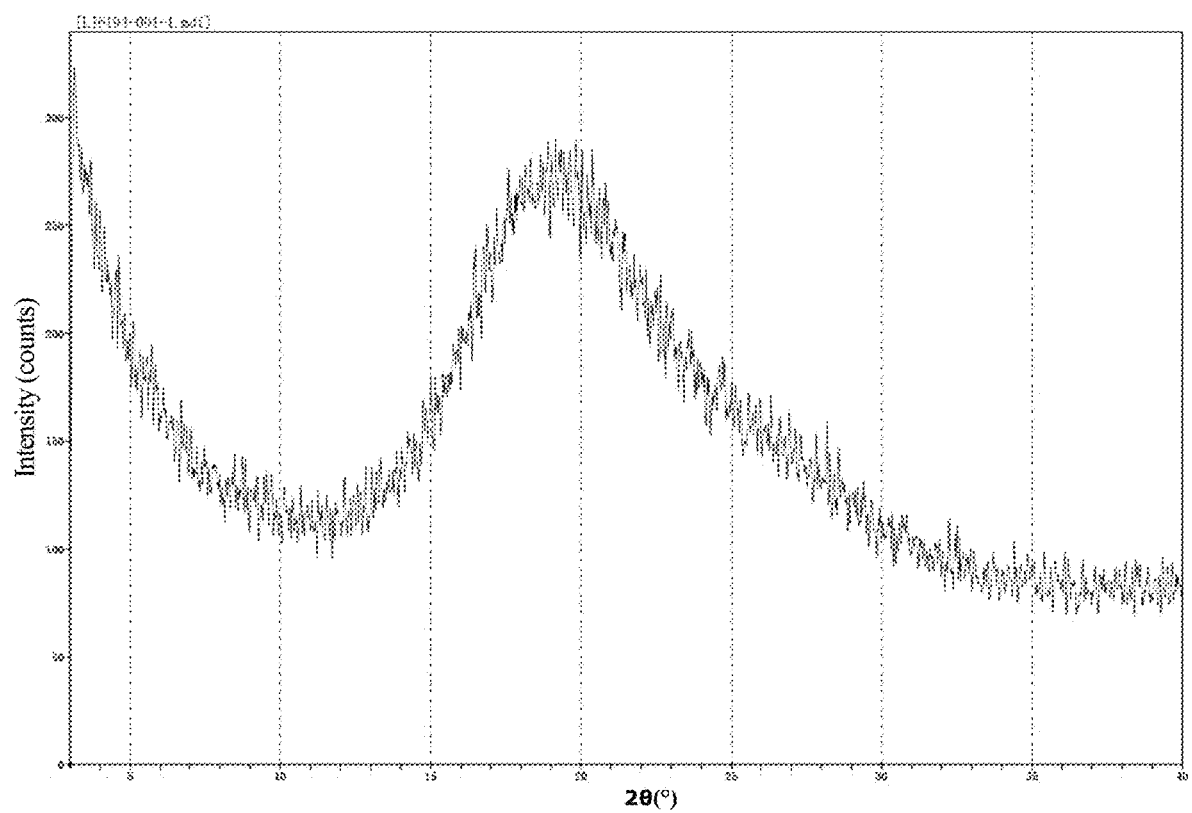
FIG. 19 is an XRPD pattern of the free base of the compound of formula (I).

The free base of the compound of formula (I) with a purity of 99.99% was prepared by referring to the preparation method of Example 1 in CN108727363A, which was inspected by XRPD and it was found that the free base of the compound of formula (I) was amorphous. The XRPD pattern is shown in FIG. 19.

Example 1 Preparation of Maleate of Compound of Formula (I)

Figure 17:
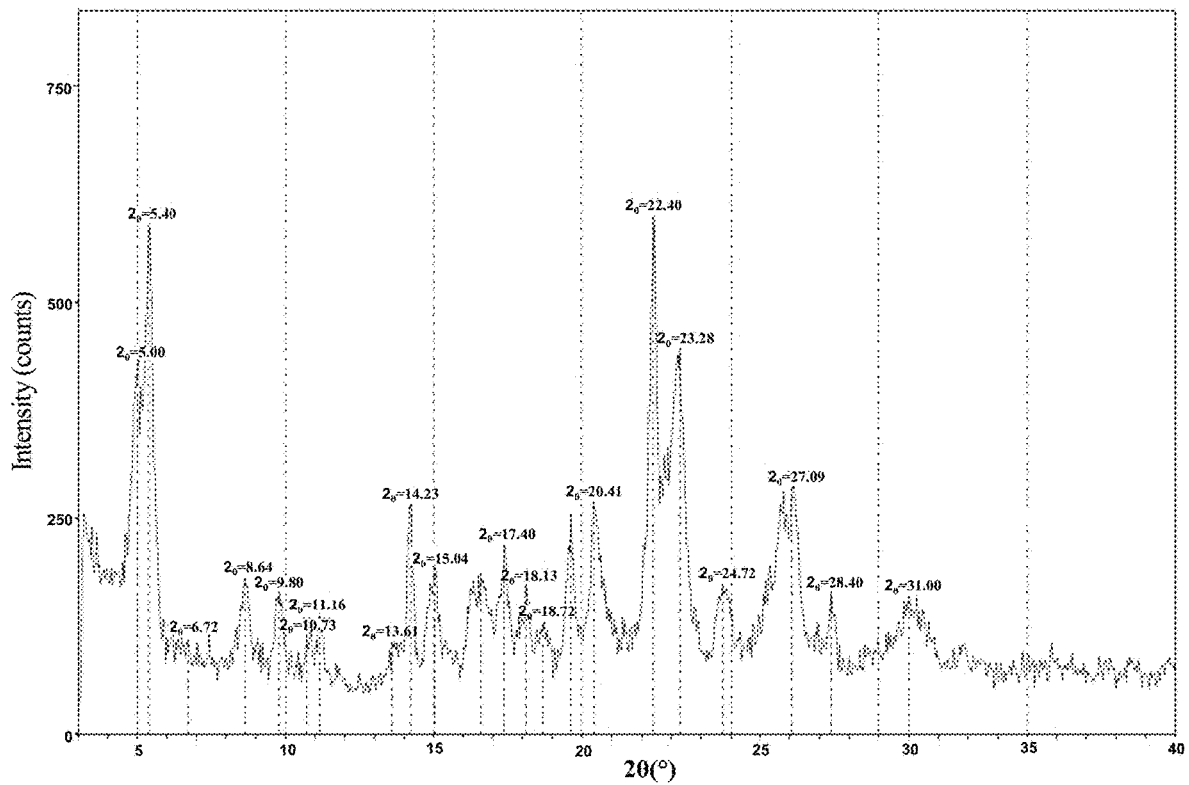
FIG. 17 is an XRPD pattern of the crystal form I of the maleate of the compound of formula (I) prepared in Example 1.
Figure 18:
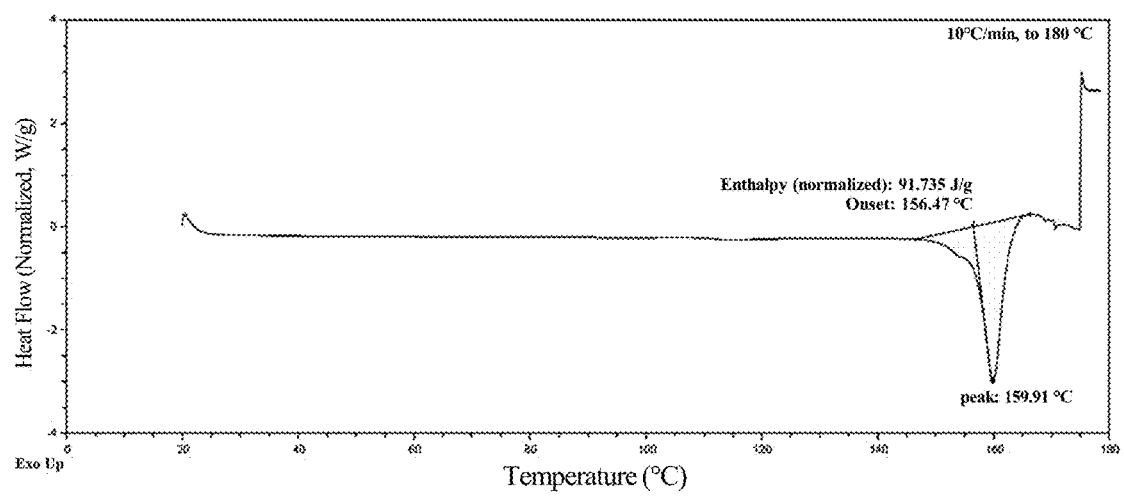
FIG. 18 is a DSC spectrum of the crystal form I of the maleate of the compound of formula (I) prepared in Example 1.

34.4 g of the free base of the compound of formula (I) was dissolved in 150 mL of acetonitrile as a free base solution for use. 300 mL of acetonitrile was added to the reaction flask, and then 16.9 g (2.2 eq) of maleic acid was added. After the mixture was heated to 75~80° C. and dissolved, the above free base solution was added dropwise. After the addition, the mixture was stirred for 1~2 h, then cooled to room temperature, further stirred for 2 hours, and filtered with suction. The filter cake was rinsed with 300 mL of acetonitrile and dry to obtain 44 g of the crystal form I of the maleate of the compound of formula (I), in which the molar ratio of the compound of formula (I) to the maleic acid is 1:2. The product was detected by XRPD and DSC. The XRPD result of the crystal form I is shown in FIG. 17 and Table 1. The DSC of the crystal form I is shown in FIG. 18.

TABLE 1

| Peak No. | 2θ[°] | d[Å] | relative intensity % |
| --- | --- | --- | --- |
| 1 | 5.00 | 17.6641 | 70.4 |
| 2 | 5.40 | 16.3505 | 100.0 |
| 3 | 6.72 | 13.1432 | 11.5 |
| 4 | 8.64 | 10.2211 | 24.5 |
| 5 | 9.80 | 9.0189 | 21.6 |
| 6 | 10.73 | 8.2394 | 12.6 |
| 7 | 11.16 | 7.9191 | 16.8 |
| 8 | 13.61 | 6.5019 | 9.6 |
| 9 | 14.23 | 6.2192 | 39.1 |
| 10 | 15.04 | 5.8860 | 26.0 |
| 11 | 16.60 | 5.3358 | 19.6 |
| 12 | 17.40 | 5.0919 | 25.7 |
| 13 | 18.13 | 4.8898 | 17.0 |
| 14 | 18.72 | 4.7372 | 9.1 |
| 15 | 19.64 | 4.5170 | 32.5 |
| 16 | 20.41 | 4.3486 | 34.9 |
| 17 | 22.40 | 3.9658 | 89.7 |
| 18 | 23.28 | 3.8186 | 65.2 |
| 19 | 24.72 | 3.5983 | 14.0 |
| 20 | 27.09 | 3.2892 | 30.9 |
| 21 | 28.40 | 3.1398 | 13.1 |
| 22 | 31.00 | 2.8826 | 12.9 |

Example 1.1 Preparation of Maleate of Compound of Formula (I)

Weigh 200 mg of the free base of the compound of formula (I), which was added into the reaction flask, and the 10 mL of acetonitrile was added to dissolve it. After the mixture was heated to 50° C., a 0.33M solution of maleic acid (2.1 eq) in acetonitrile was added dropwise while stirring. After stirred for 1 hour, the mixture was cooled to room temperature, further stirred for 1 hour, and then filtered. The filter cake was rinsed with a small amount of acetonitrile and dried to obtain 255 mg of off-white solid with a yield of 88.2%. The product was detected by XRPD and DSC. It is determined that the product is the crystal form I of the maleate salt of the compound of formula (I), in which the molar ratio of the compound of formula (I) to the maleic acid is 1:2. The XRPD result is basically shown in FIG. 17 and Table 1. The DSC is basically shown in FIG. 18.
$^1$H NMR (400 MHz, DMSO-d6) δ 8.35 (s, 1H), 8.22 (s, 1H), 8.12 (t, J=6.3 Hz, 1H), 7.99 (s, 1H), 7.36 (s, 1H), 7.05 (s, 1H), 6.77 (d, J=7.4 Hz, 1H), 6.15 (s, 4H), 3.92 (m, 2H), 3.67 (d, J=6.3 Hz, 2H), 3.60 (s, 1H), 3.57~3.41 (m, 5H), 3.35 (s, 3H), 3.13 (s, 1H), 2.05 (d, J=10.9 Hz, 4H), 1.87 (d, J=13.5 Hz, 2H), 1.73~1.66 (m, 2H), 1.50~1.37 (m, 2H), 1.28 (m, 2H), 1.21 (d, J=6.4 Hz, 3H).

Example 2 Preparation of Crystal Form 1 of Maleate of Compound of Formula (I)

Figure 2:
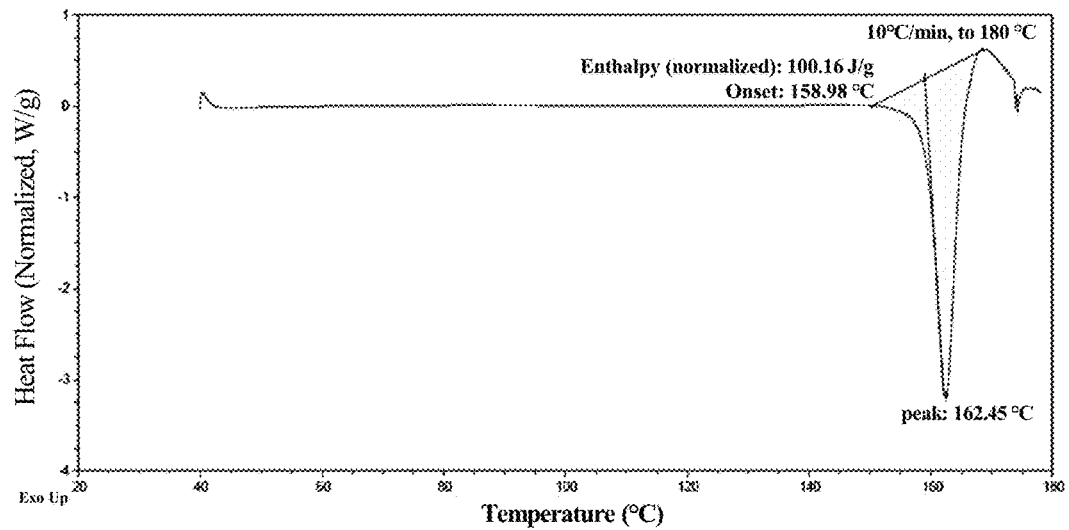
FIG. 2 is a DSC spectrum of the crystal form 1 of the maleate of the compound of formula (I) prepared in Example 2.
Figure 3:
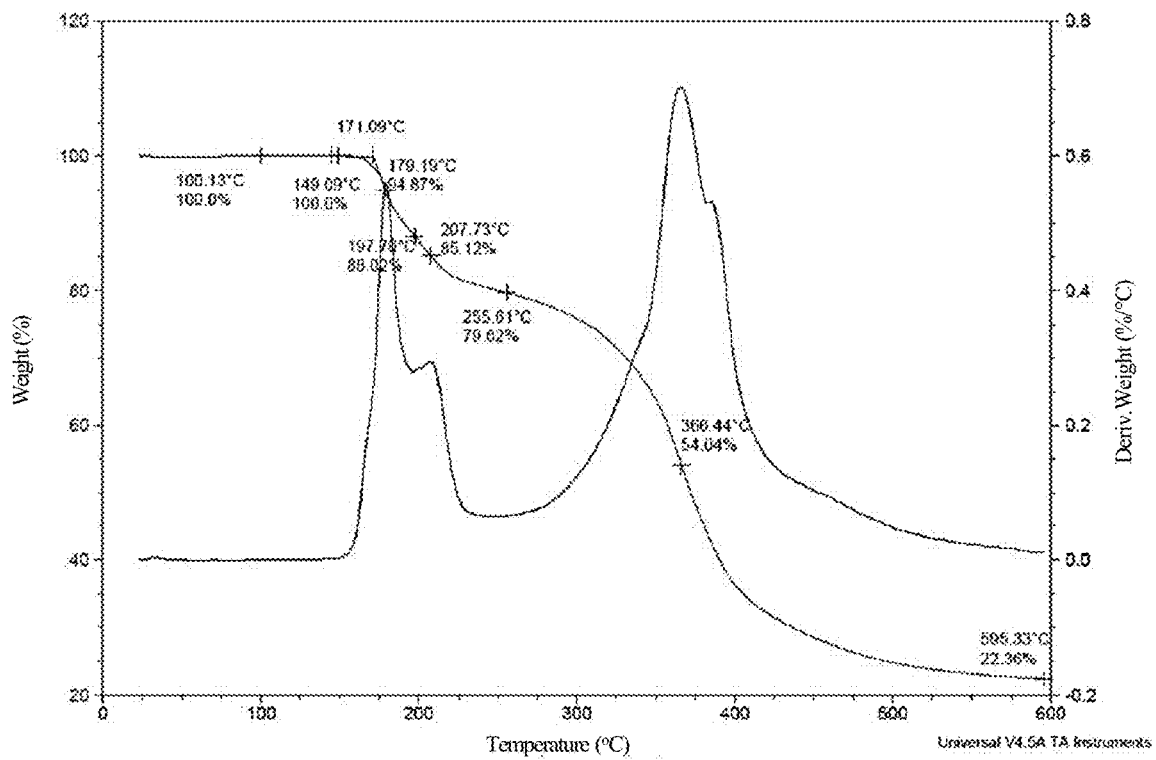
FIG. 3 is a TGA spectrum of the crystal form 1 of the maleate of the compound of formula (I) prepared in Example 2.
Figure 4:
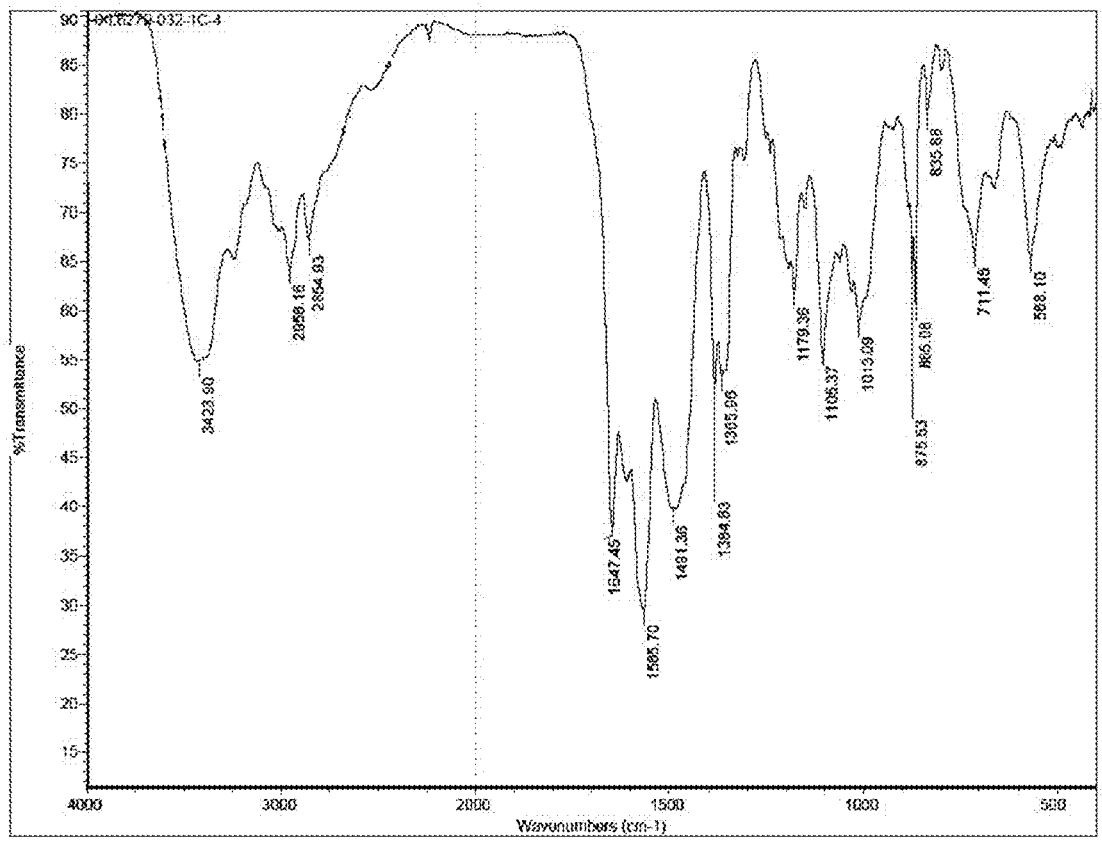
FIG. 4 is an IR spectrum of the crystal form 1 of the maleate of the compound of formula (I) prepared in Example 2.

34 g of the maleate of the compound of formula (I) prepared in Example 1 was added into the reaction flask, and 340 ml of a mixed solvent of acetonitrile and water (the volume ratio is 20:1) was added to the reaction flask. The reaction system was heated under the protection of nitrogen to reflux and clear (80-85° C.). The reaction system was cooled to 75° C. and crystallized for 1-2 h. Then the system was cooled naturally to 2-10° C. and filtered with suction. The solid was dried at 60° C. under vacuum to obtain the crystal form 1 of the maleate of the compound of formula (I) with a yield of 80%. The melting point is 156-160° C. The purity is 99.91%. The product is detected by XRPD, DSC, TGA and IR. The XRPD result of the crystal form 1 is shown in FIG. 1 and Table 2. The DSC of the crystal form 1 is shown in FIG. 2. The TGA of the crystal form 1 is shown in FIG. 3. The IR of the crystal form 1 is shown in FIG. 4. $^1$H NMR (600 MHz, DMSO-d6) δ 8.38 (s, 1H), 8.25 (s, 1H), 8.12 (t, J=6.3 Hz, 1H), 8.00 (s, 1H), f7.37 (s, 1H), 7.06 (s, 1H), 6.78 (s, 1H), 6.16 (s, 4H), 3.92 (m, 2H), 3.67 (d, J=6.1 Hz, 2H), 3.62 (s, 1H), 3.56~3.42 (m, 5H), 3.35 (s, 3H), 3.14 (s, 1H), 2.05 (m, 4H), 1.87 (d, J=13.8 Hz, 2H), 1.73~1.68 (m, 2H), 1.53~1.39 (m, 2H), 1.28 (m, 2H), 1.22 (d, J=6.5 Hz, 3H).

TABLE 2

| Peak No. | 2θ[°] | d[Å] | relative intensity % |
|---|---|---|---|
| 1 | 5.02 | 17.5866 | 13.1 |
| 2 | 5.48 | 16.1183 | 48.9 |
| 3 | 8.78 | 10.0656 | 4.6 |
| 4 | 9.12 | 9.6905 | 1.6 |
| 5 | 9.86 | 8.9624 | 16.9 |
| 6 | 10.88 | 8.1283 | 5.6 |
| 7 | 11.22 | 7.8797 | 13.7 |
| 8 | 13.66 | 6.4772 | 2.5 |
| 9 | 14.26 | 6.2063 | 28.1 |
| 10 | 15.06 | 5.8778 | 19.4 |
| 11 | 16.28 | 5.4411 | 3.4 |
| 12 | 16.82 | 5.2672 | 10.8 |
| 13 | 17.48 | 5.0701 | 5.5 |
| 14 | 18.18 | 4.8759 | 9.0 |
| 15 | 18.72 | 4.7362 | 1.1 |
| 16 | 19.68 | 4.5073 | 27.9 |
| 17 | 20.10 | 4.4141 | 3.7 |
| 18 | 20.50 | 4.3289 | 7.9 |
| 19 | 21.40 | 4.1487 | 1.4 |
| 20 | 22.44 | 3.9590 | 100.0 |
| 21 | 22.82 | 3.8941 | 7.4 |
| 22 | 23.24 | 3.8244 | 18.2 |
| 23 | 24.90 | 3.5733 | 20.0 |
| 24 | 26.07 | 3.4159 | 4.0 |
| 25 | 26.76 | 3.3287 | 11.5 |
| 26 | 27.16 | 3.2805 | 10.9 |
| 27 | 28.10 | 3.1727 | 1.5 |
| 28 | 28.48 | 3.1315 | 5.1 |
| 29 | 29.84 | 2.9915 | 2.7 |
| 30 | 30.30 | 2.9475 | 3.4 |
| 31 | 30.86 | 2.8950 | 5.9 |
| 32 | 31.42 | 2.8447 | 4.6 |
| 33 | 31.72 | 2.8186 | 2.7 |
| 34 | 32.66 | 2.7396 | 1.0 |
| 35 | 34.94 | 2.5657 | 2.3 |

TABLE 2-continued

| Peak No. | 2θ[°] | d[Å] | relative intensity % |
|---|---|---|---|
| 36 | 35.24 | 2.5447 | 2.0 |
| 37 | 35.92 | 2.4980 | 2.0 |
| 38 | 36.44 | 2.4636 | 2.8 |

Example 2.1 Preparation of Crystal Form 1 of Maleate of Compound of Formula (I)

200 mg of the maleate of the compound of formula (I) prepared in Example 1 was added into the reaction flask, and 10 ml of a mixed solvent of acetonitrile and water (the volume ratio is 4:1) was added into the reaction flask, and the reaction system was heated under the protection of nitrogen to reflux and clear (80-85° C.). The reaction system was cooled to 75° C. and crystallized for 1-2 h. Then the system was cooled naturally to room temperature and filtered with suction. The solid was rinsed with isopropanol and dried at 45° C. under vacuum to obtain a product with a yield of 81%. It was determined that the product is the crystal form 1 of the maleate of the compound of formula (I) by XRPD and DSC. The XRPD result is basically shown in FIG. 1 and Table 2. The DSC is basically shown in FIG. 2.

Example 2.2 Preparation of Crystal Form 1 of Maleate of Compound of Formula (I)

100 mg of the maleate of the compound of formula (I) prepared in Example 1.1 was added into 1-2 ml of acetonitrile. The mixture was kept at a temperature of 0° C. and stirred for 24 hours. After that the reaction solution was filtered. The solid was collected and dried to obtain the product. The purity is 99.99%. It is determined that the product is the crystal form 1 of the maleate of the compound of formula (I) by XRPD and DSC. The XRPD result is basically shown in FIG. 1 and Table 2. The DSC is basically shown in FIG. 2.

Example 2.3 Preparation of Crystal Form 1 of Maleate of Compound of Formula (I)

100 mg of the maleate of the compound of formula (I) prepared in Example 1.1 was added into 1-2 ml of acetonitrile. The mixture was kept at a temperature of 25° C. and stirred for 24 hours. After that the reaction solution was filtered. The solid was collected and dried to obtain the product. The purity is 99.99%. It is determined that the product is the crystal form 1 of the maleate of the compound of formula (I) by XRPD and DSC. The XRPD result is basically shown in FIG. 1 and Table 2. The DSC is basically shown in FIG. 2.

Example 2.4 Preparation of Crystal Form 1 of Maleate of Compound of Formula (I)

100 mg of the maleate of the compound of formula (I) prepared in Example 1.1 was added into 1-2 ml of a mixed solvent of acetonitrile and water (the volume ratio is 10:1). The mixture was kept at a temperature of 0° C. and stirred for 24 hours. After that the reaction solution was filtered. The solid was collected and dried to obtain the product. The purity is 99.91%. It is determined that the product is the crystal form 1 of the maleate of the compound of formula (I)

by XRPD and DSC. The XRPD result is basically shown in FIG. 1 and Table 2. The DSC is basically shown in FIG. 2.

Example 3 Preparation of Crystal Form 2 of Maleate of Compound of Formula (I)

Figure 5:
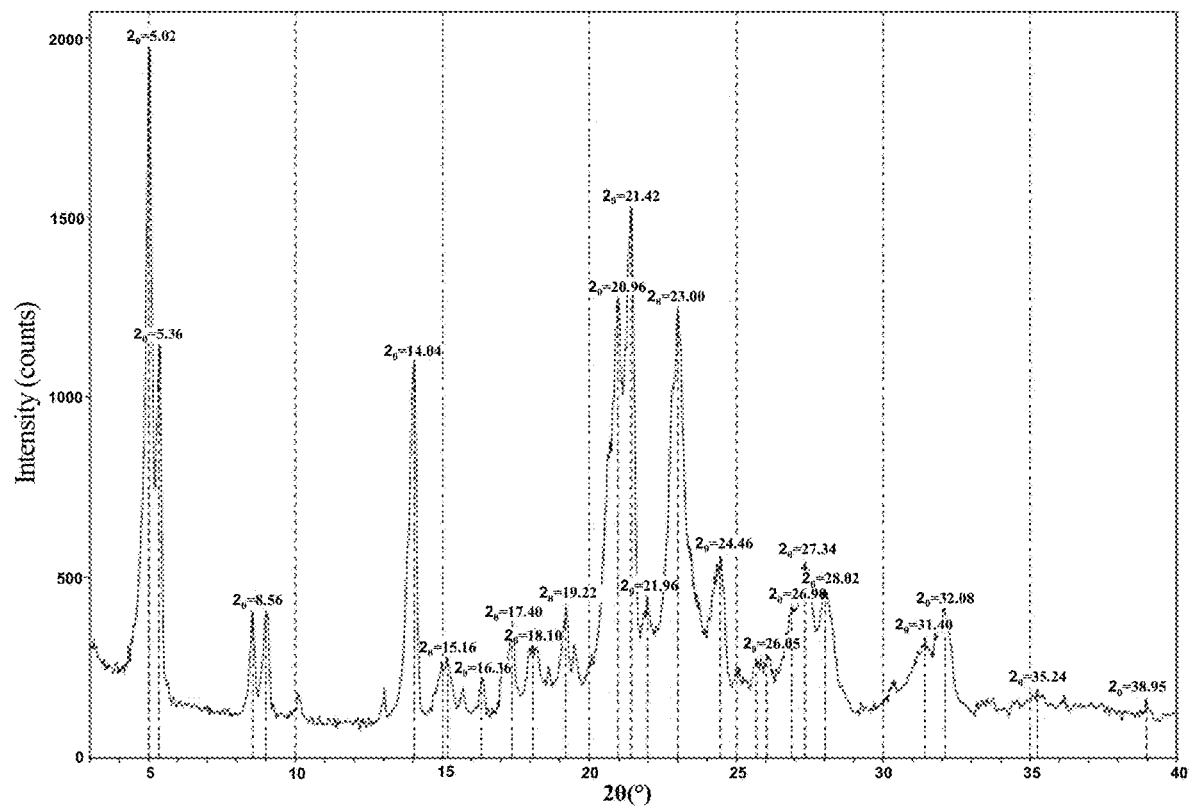
FIG. 5 is an XRPD pattern of the crystal form 2 of the maleate of the compound of formula (I) prepared in Example 3.
Figure 6:
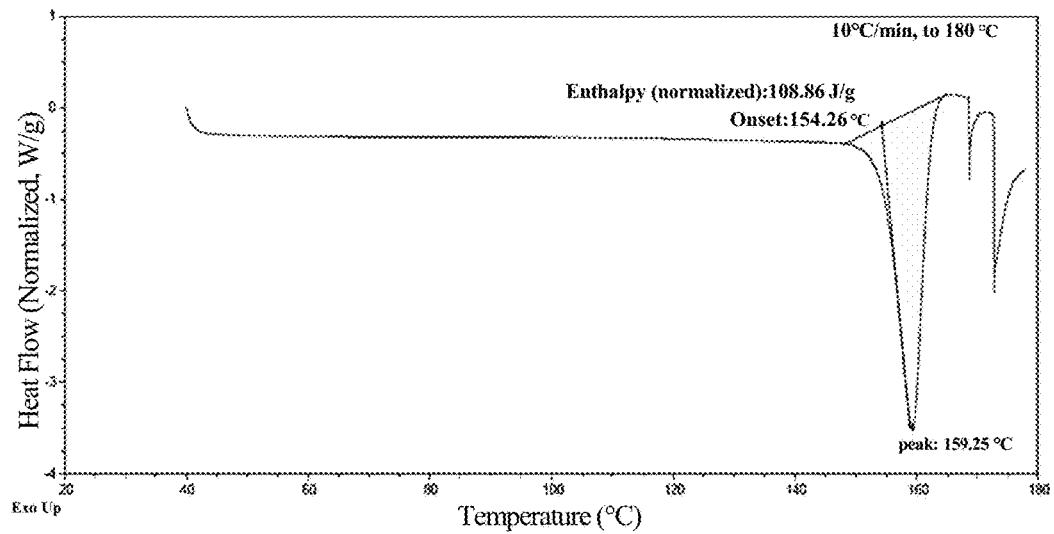
FIG. 6 is a DSC spectrum of the crystal form 2 of the maleate of the compound of formula (I) prepared in Example 3.
Figure 7:
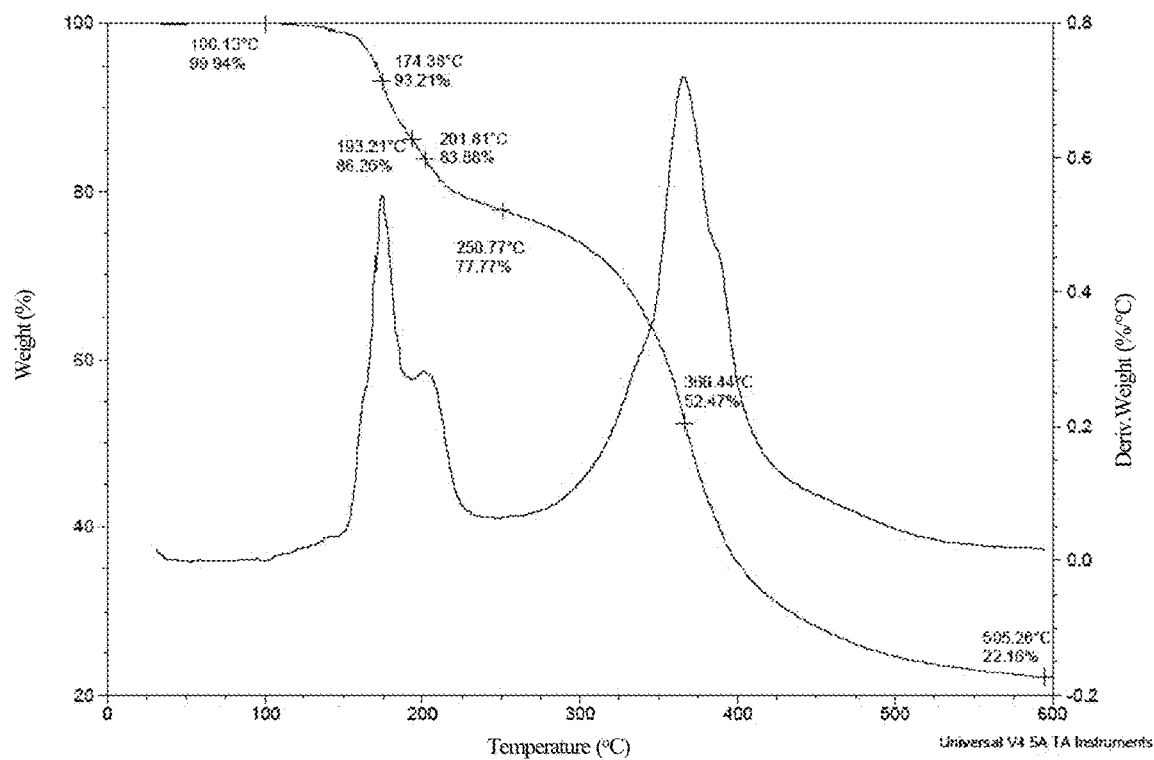
FIG. 7 is a TGA spectrum of the crystal form 2 of the maleate of the compound of formula (I) prepared in Example 3.
Figure 8:
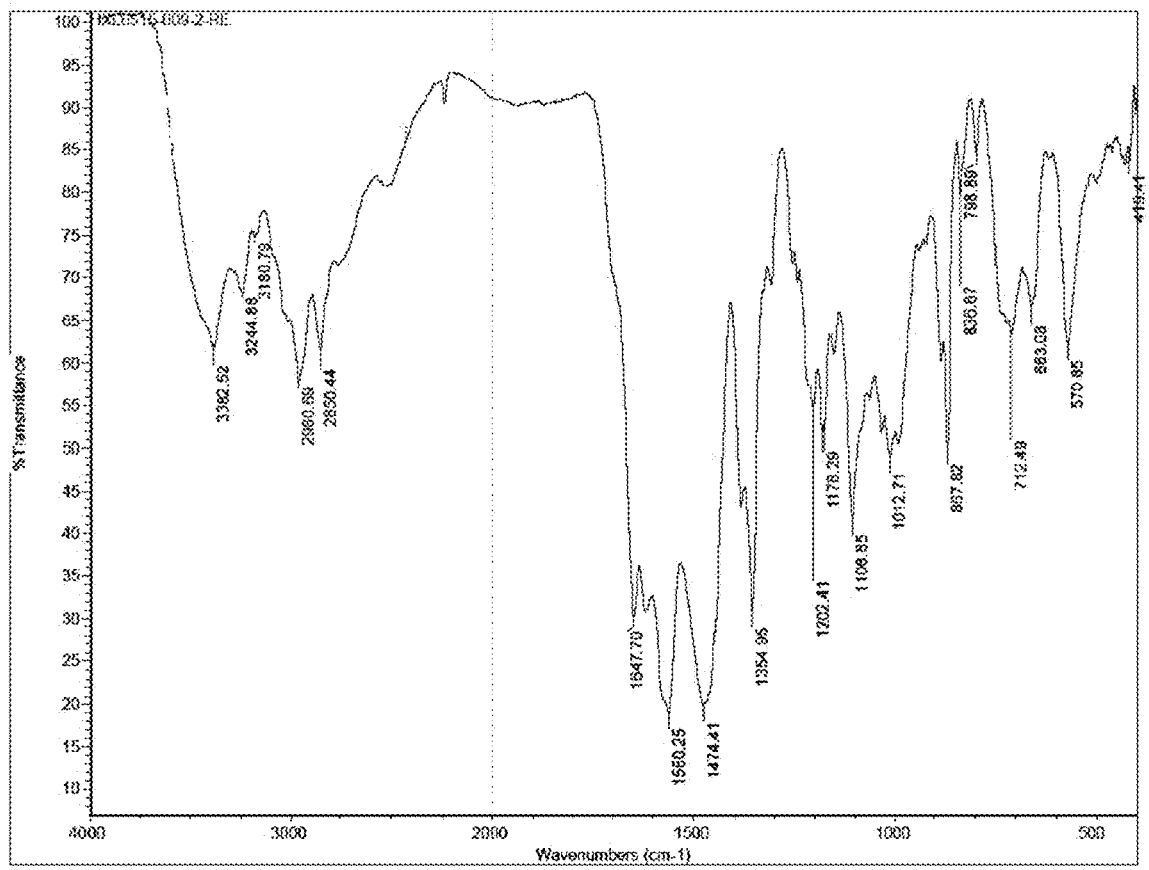
FIG. 8 is an IR spectrum of the crystal form 2 of the maleate of the compound of formula (I) prepared in Example 3.

10 g of the maleate of the compound of formula (I) prepared in Example 1 was added into 100 ml of methyl tert-butyl ether. Under the protection of nitrogen, the mixture was kept at a temperature of 25° C. and stirred overnight. After that the reaction solution was filtered. The solid was collected and spin-dried at 40-50° C. to obtain the crystal form 2 of the maleate of the compound of formula (I) with a yield of 70%. The melting point is 152-156° C. The purity is 99.13%. The product is detected by XRPD, DSC, TGA and IR. The XRPD result of the crystal form 2 is shown in FIG. 5 and Table 3. The DSC of the crystal form 2 is shown in FIG. 6. The TGA of the crystal form 2 is shown in FIG. 7. The IR of the crystal form 2 is shown in FIG. 8.

TABLE 3

| Peak No. | 2θ[°] | d[Å] | relative intensity % |
|---|---|---|---|
| 1 | 5.02 | 17.5879 | 100.0 |
| 2 | 5.36 | 16.4713 | 54.5 |
| 3 | 8.56 | 10.3219 | 15.7 |
| 4 | 9.00 | 9.8162 | 15.7 |
| 5 | 14.04 | 6.3028 | 53.6 |
| 6 | 15.16 | 5.8396 | 8.5 |
| 7 | 16.36 | 5.4132 | 5.3 |
| 8 | 17.40 | 5.0929 | 11.8 |
| 9 | 18.10 | 4.8974 | 6.9 |
| 10 | 19.22 | 4.6141 | 11.8 |
| 11 | 20.96 | 4.2348 | 53.4 |
| 12 | 21.42 | 4.1451 | 67.1 |
| 13 | 21.96 | 4.0436 | 5.3 |
| 14 | 23.00 | 3.8637 | 49.1 |
| 15 | 24.46 | 3.6364 | 19.9 |
| 16 | 25.68 | 3.4662 | 3.8 |
| 17 | 26.05 | 3.4184 | 3.7 |
| 18 | 26.90 | 3.3118 | 10.7 |
| 19 | 27.34 | 3.2594 | 15.5 |
| 20 | 28.02 | 3.1818 | 18.7 |
| 21 | 31.40 | 2.8465 | 7.3 |
| 22 | 32.08 | 2.7879 | 15.6 |
| 23 | 35.24 | 2.5449 | 3.3 |
| 24 | 38.95 | 2.3107 | 3.0 |

Example 3.1 Preparation of Crystal Form 2 of Maleate of Compound of Formula (I)

100 mg of the maleate of the compound of formula (I) prepared in Example 1.1 was added into 1-2 ml of methyl tert-butyl ether. The mixture was kept at a temperature of 0° C. and stirred for 24 hours. After that the reaction solution was filtered. The solid was collected and dried to obtain the product. The purity is 99.99%. It is determined that the product is the crystal form 2 of the maleate of the compound of formula (I) by XRPD and DSC. The XRPD result is basically shown in FIG. 5 and Table 3. The DSC is basically shown in FIG. 6.

Example 3.2 Preparation of Crystal Form 2 of Maleate of Compound of Formula (I)

100 mg of the maleate of the compound of formula (I) prepared in Example 1.1 was added into 1-2 ml of methyl tert-butyl ether. The mixture was kept at a temperature of 50° C. and stirred for 24 hours. After that the reaction solution was filtered. The solid was collected and dried to obtain the product. The purity is 99.88%. It is determined that the product is the crystal form 2 of the maleate of the compound of formula (I) by XRPD and DSC. The XRPD result is basically shown in FIG. 5 and Table 3. The DSC is basically shown in FIG. 6.

Example 3.3 Preparation of Crystal Form 2 of Maleate of Compound of Formula (I)

100 mg of the maleate of the compound of formula (I) prepared in Example 1.1 was added into 1-2 ml of ethyl acetate. The mixture was kept at a temperature of 50° C. and stirred for 24 hours. After that the reaction solution was filtered. The solid was collected and dried to obtain the product. The purity is 99.81%. It is determined that the product is the crystal form 2 of the maleate of the compound of formula (I) by XRPD and DSC. The XRPD result is basically shown in FIG. 5 and Table 3. The DSC is basically shown in FIG. 6.

Example 4 Preparation of Crystal Form 3 of Maleate of Compound of Formula (I)

Figure 9:
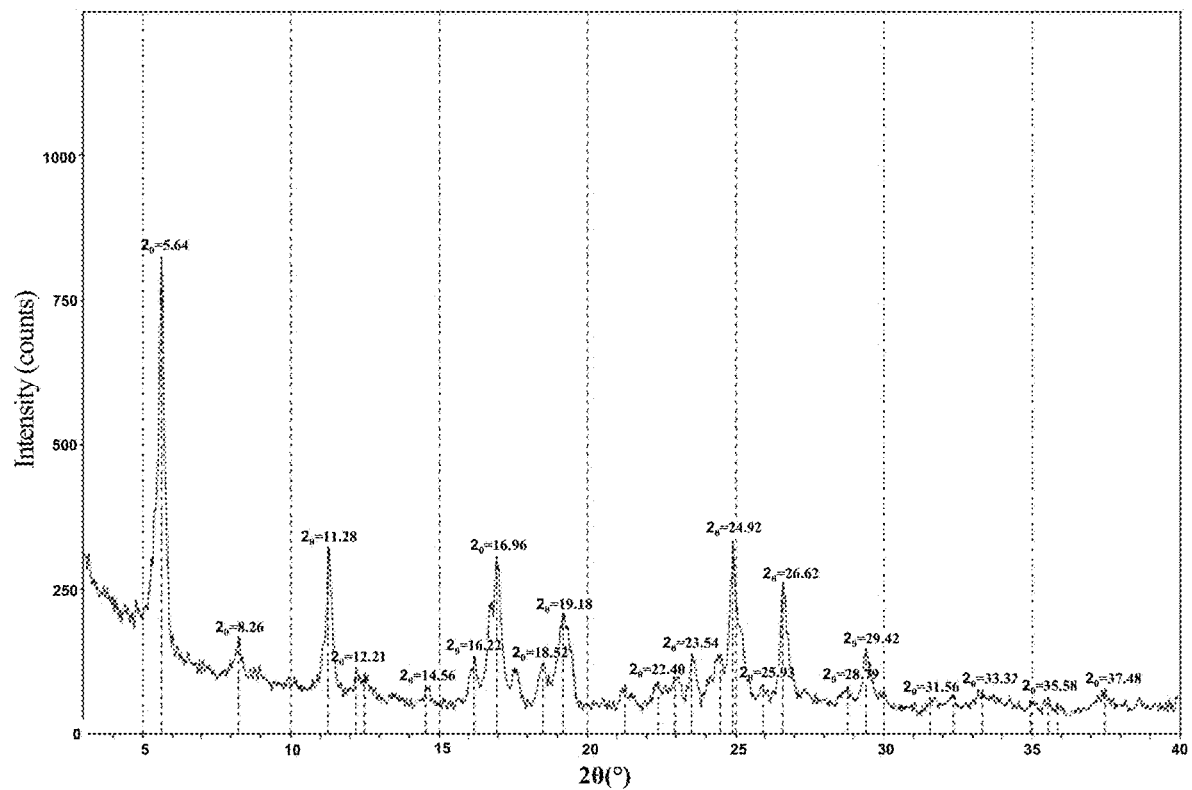
FIG. 9 is an XRPD pattern of the crystal form 3 of the maleate of the compound of formula (I) prepared in Example 4.
Figure 10:
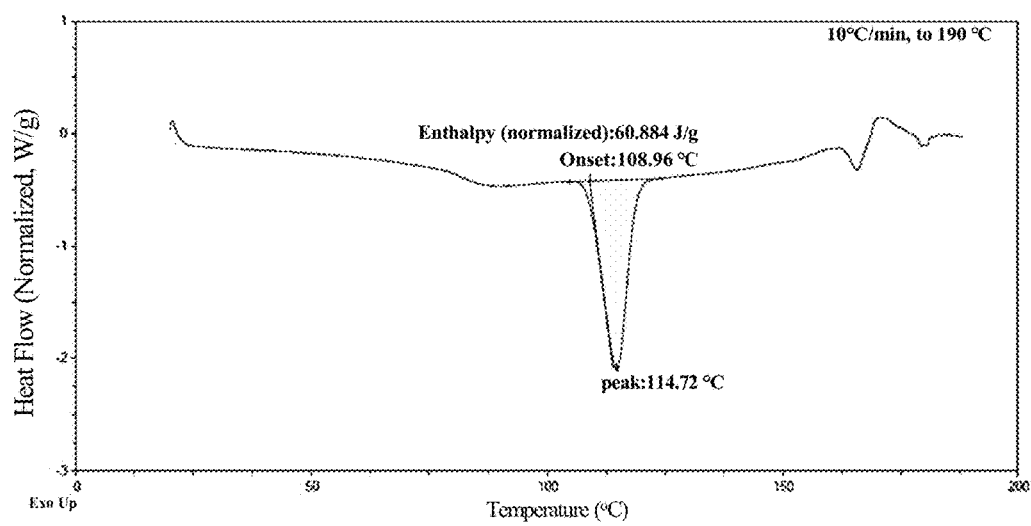
FIG. 10 is a DSC spectrum of the crystal form 3 of the maleate of the compound of formula (I) prepared in Example 4.

100 mg of the maleate of the compound of formula (I) prepared in Example 1.1 was added into 1-2 ml of a mixed solvent of acetone and water (the volume ratio of acetone and water was 10:1). The mixture was stirred for 24 hours at 50° C. After that the reaction solution was filtered. The solid was collected and dried to obtain the crystal form 3 of the maleate of the compound of formula (I) with a yield of 50%. The purity is 99.99%. The product is detected by XRPD and DSC. The XRPD result of the crystal form 3 is shown in FIG. 9 and Table 4. The DSC of the crystal form 3 is shown in FIG. 10.

TABLE 4

| Peak No. | 2θ[°] | d[Å] | relative intensity % |
|---|---|---|---|
| 1 | 5.64 | 15.6566 | 100.0 |
| 2 | 8.26 | 10.6970 | 9.6 |
| 3 | 11.28 | 7.8370 | 35.4 |
| 4 | 12.21 | 7.2452 | 5.8 |
| 5 | 12.50 | 7.0732 | 4.4 |
| 6 | 14.56 | 6.0785 | 4.6 |
| 7 | 16.22 | 5.4603 | 12.1 |
| 8 | 16.96 | 5.2234 | 35.5 |
| 9 | 18.52 | 4.7869 | 10.1 |
| 10 | 19.18 | 4.6234 | 22.5 |
| 11 | 21.28 | 4.1720 | 5.7 |
| 12 | 22.40 | 3.9662 | 5.5 |
| 13 | 22.98 | 3.8676 | 8.8 |
| 14 | 23.54 | 3.7763 | 10.5 |
| 15 | 24.50 | 3.6306 | 9.9 |
| 16 | 24.92 | 3.5704 | 38.4 |
| 17 | 25.93 | 3.4327 | 3.4 |
| 18 | 26.62 | 3.3459 | 28.9 |
| 19 | 28.79 | 3.0981 | 3.6 |
| 20 | 29.42 | 3.0336 | 14.0 |
| 21 | 30.02 | 2.9743 | 3.2 |
| 22 | 31.56 | 2.8325 | 2.4 |
| 23 | 32.38 | 2.7629 | 3.1 |
| 24 | 33.32 | 2.6867 | 3.9 |
| 25 | 34.96 | 2.5645 | 2.3 |
| 26 | 35.58 | 2.5214 | 3.4 |
| 27 | 35.88 | 2.5010 | 2.3 |
| 28 | 37.48 | 2.3976 | 5.0 |

Example 5 Preparation of Crystal Form 4 of Maleate of Compound of Formula (I)

100 mg of the maleate of the compound of formula (I) prepared in Example 1 was added into 1-2 ml of a mixed solvent of ethanol and water (the volume ratio of ethanol and water was 10:1). The mixture was stirred for 24 hours at 25° C. After that the reaction solution was filtered.

Figure 11:
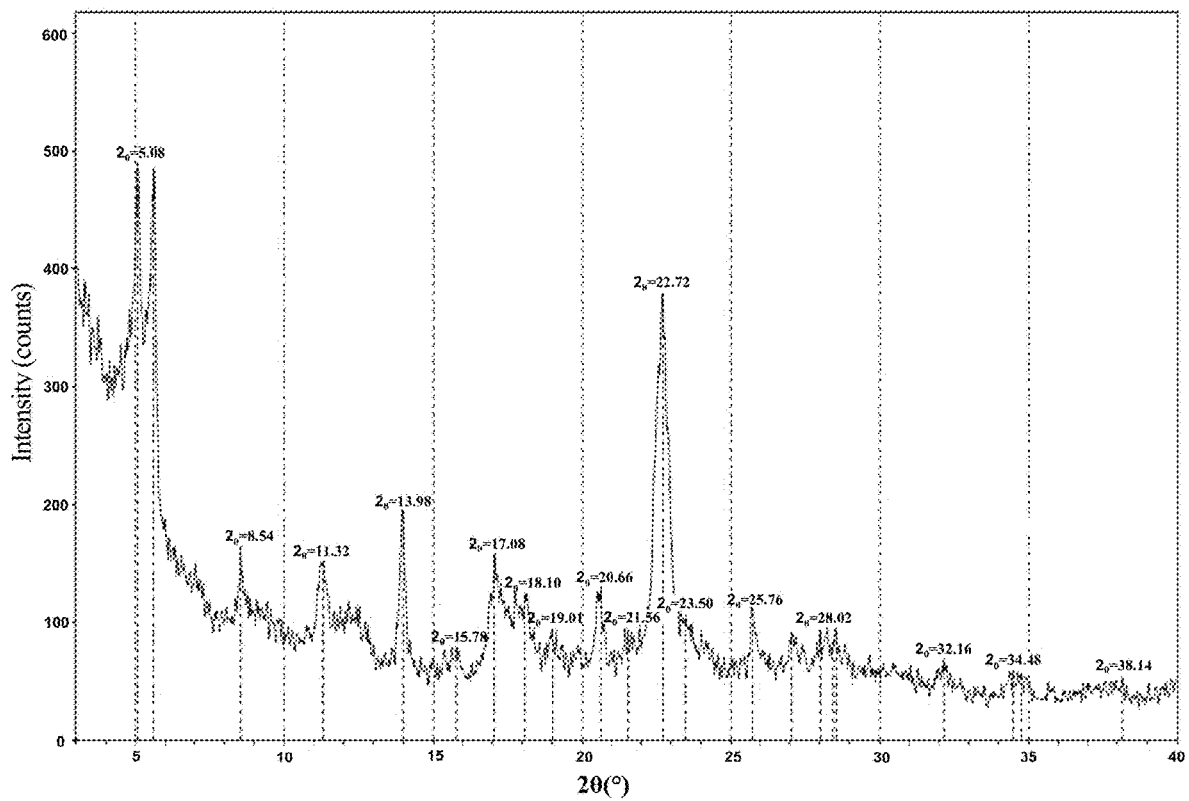
FIG. 11 is an XRPD pattern of the crystal form 4 of the maleate of the compound of formula (I) prepared in Example 5.
Figure 12:
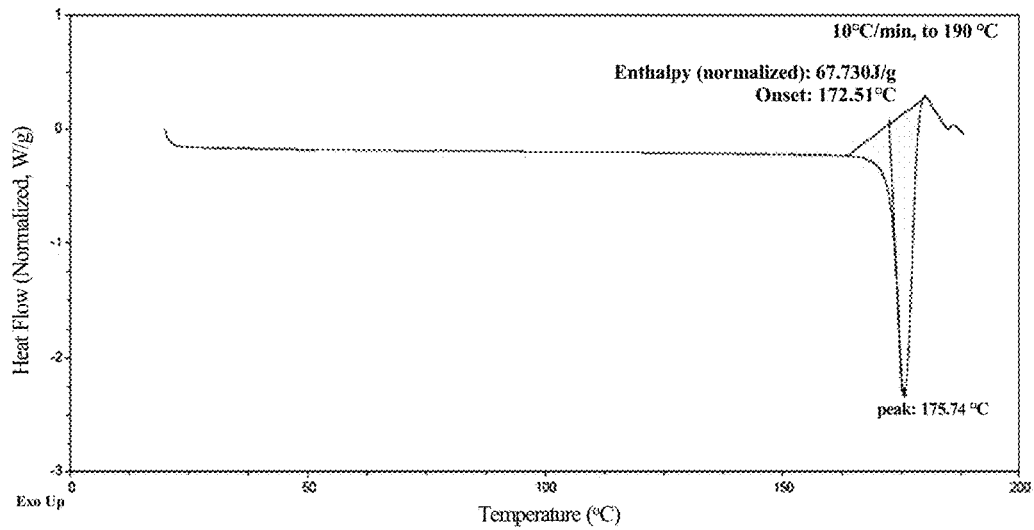
FIG. 12 is a DSC spectrum of the crystal form 4 of the maleate of the compound of formula (I) prepared in Example 5.

The solid was collected and dried to obtain the crystal form 4 of the maleate of the compound of formula (I) with a yield of 45%. The purity is 99.99%. The melting point is 171-176° C. The product is detected by XRPD and DSC. The XRPD result of the crystal form 4 is shown in FIG. 11 and Table 5. The DSC of the crystal form 4 is shown in FIG. 12.

TABLE 5

| Peak No. | 2θ[°] | d[Å] | relative intensity % |
|---|---|---|---|
| 1 | 5.08 | 17.3812 | 95.4 |
| 2 | 5.62 | 15.7139 | 100.0 |
| 3 | 8.54 | 10.3433 | 18.8 |
| 4 | 11.32 | 7.8119 | 17.2 |
| 5 | 13.98 | 6.3303 | 39.4 |
| 6 | 15.78 | 5.6122 | 6.5 |
| 7 | 17.08 | 5.1874 | 29.7 |
| 8 | 18.10 | 4.8967 | 19.8 |
| 9 | 19.01 | 4.6635 | 7.2 |
| 10 | 20.66 | 4.2963 | 18.6 |
| 11 | 21.56 | 4.1193 | 6.5 |
| 12 | 22.72 | 3.9108 | 87.3 |
| 13 | 23.50 | 3.7827 | 12.0 |
| 14 | 25.76 | 3.4560 | 14.7 |
| 15 | 27.08 | 3.2898 | 9.0 |
| 16 | 28.02 | 3.1822 | 9.2 |
| 17 | 28.45 | 3.1352 | 7.5 |
| 18 | 28.55 | 3.1237 | 9.9 |
| 19 | 32.16 | 2.7810 | 7.9 |
| 20 | 34.48 | 2.5988 | 7.0 |
| 21 | 34.76 | 2.5791 | 4.9 |
| 22 | 38.14 | 2.3574 | 4.4 |

Example 6 Preparation of Crystal Form 4 of Maleate of Compound of Formula (I)

100 mg of the maleate of the compound of formula (I) prepared in Example 1 was added into 1-2 ml of a mixed solvent of isopropanol and water (the volume ratio of isopropanol and water was 10:1). The mixture was stirred for 24 hours at 25° C. After that the reaction solution was filtered. The solid was collected and dried to obtain the crystal form 4 of the maleate of the compound of formula (I) with a yield of 38%. The purity is 99.92%. It is determined by XRPD and DSC. The XRPD result is basically shown in FIG. 11. The DSC is basically shown in FIG. 12.

Example 7 Preparation of Crystal Form 4 of Maleate of Compound of Formula (I)

100 mg of the maleate of the compound of formula (I) prepared in Example 1 was added into 1-2 ml of ethanol. The mixture was stirred for 24 hours at 50° C. After that the reaction solution was filtered. The solid was collected and dried to obtain the crystal form 4 of the maleate of the compound of formula (I) with a yield of 42%. The purity is 99.97%. It is determined by XRPD and DSC. The XRPD result is basically shown in FIG. 11. The DSC is basically shown in FIG. 12.

Example 8 Preparation of Crystal Form 4 of Maleate of Compound of Formula (I)

100 mg of the maleate of the compound of formula (I) prepared in Example 1 was added into 1-2 ml of isopropanol. The mixture was stirred for 24 hours at 50° C. After that the reaction solution was filtered. The solid was collected and dried to obtain the crystal form 4 of the maleate of the compound of formula (I) with a yield of 35%. The purity is 99.99%. It is determined by XRPD and DSC. The XRPD result is basically shown in FIG. 11. The DSC is basically shown in FIG. 12.

Example 9 Preparation of Crystal Form a of Fumarate of Compound of Formula (I)

Figure 13:
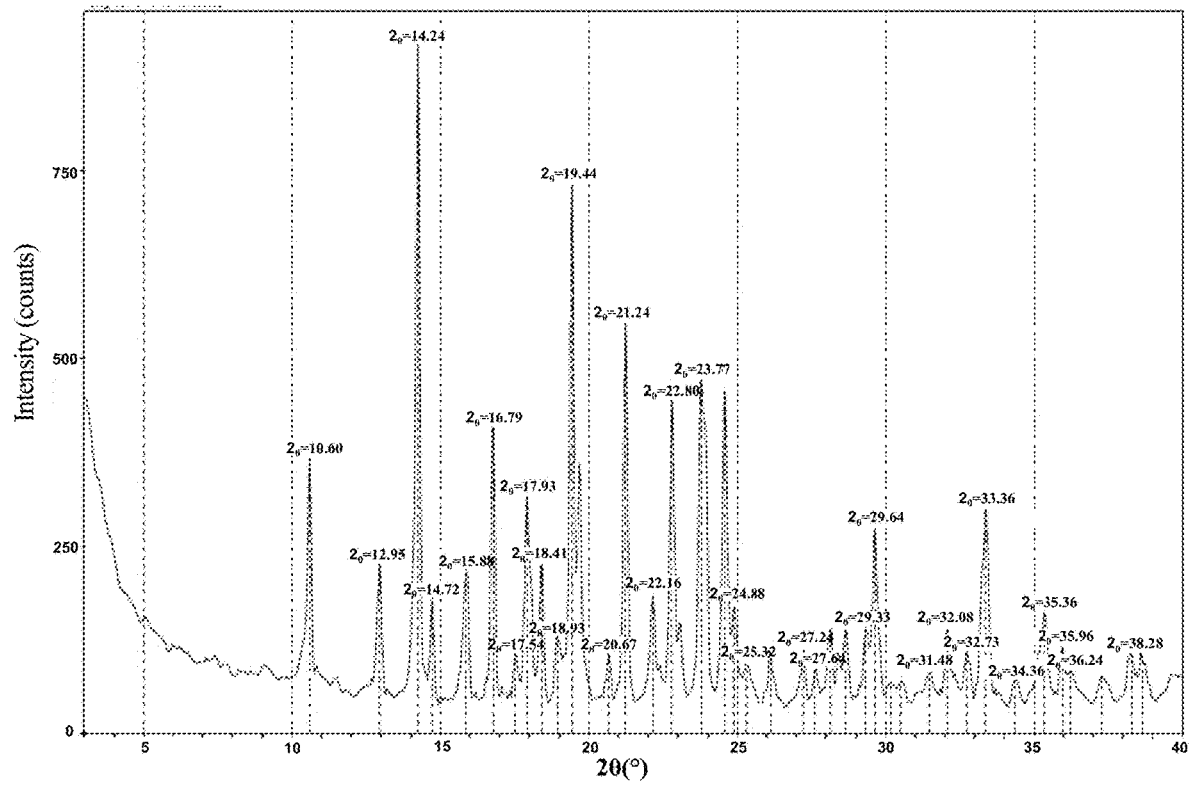
FIG. 13 is an XRPD pattern of the crystal form A of the fumarate of the compound of formula (I) prepared in Example 9.
Figure 14:
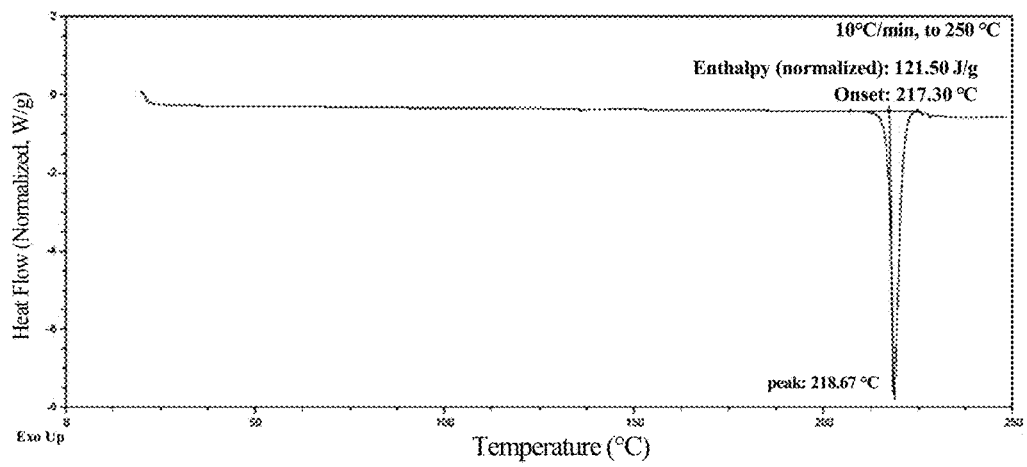
FIG. 14 is a DSC spectrum of the crystal form A of the fumarate of the compound of formula (I) prepared in Example 9.

2 g of the free base of the compound of formula (I) was dissolved in 30 mL of acetonitrile to obtain a clear solution of the free base in acetonitrile. The solution was kept in a 50° C. water bath and 9.236 mL of a 0.25M fumaric acid solution (268 mg, 0.6 eq) in ethanol was added dropwise while stirring. Then a solid precipitated gradually and the system was kept at 50° C. and stirred for 0.5 hours. After the heating was stopped, the system was cooled to room temperature naturally and further stirred for 1 hour, and then filtered. The filter cake was rinsed with 40 mL of acetonitrile, and dried at 50° C. under vacuum to obtain the crystal form A of the fumarate of the compound of formula (I) with a yield of 94.0%, in which the molar ratio of the compound of formula (I) to the fumaric acid is 1.0.5. The melting point is 217-218° C. The purity is 99.38%. The product is detected by XRPD and DSC. The XRPD result of the crystal form A is shown in FIG. 13 and Table 6. The DSC of the crystal form A is shown in FIG. 14. $^1$H NMR (400 MHz, DMSO-d6) δ 8.10 (t, J=6.4 Hz 1H), 7.95 (s, 1H), 7.31 (s, 1H), 6.99 (s, 1H), 6.65 (d, J=7.6 Hz, 1H), 6.39 (s, 1H), 3.90 (m, 2H), 3.62 (d, J=6.1 Hz, 2H), 3.55 (s, 1H), 3.47~3.39 (m, 2H), 3.31~3.25 (m, 2H), 3.23 (s, 3H), 3.13 (m, 1H), 2.70 (s, 1H), 1.95~1.82 (m, 6H), 1.66~1.62 (m, 2H), 1.26~1.17 (m, 4H), 1.00 (d, J=6.4 Hz, 3H).

TABLE 6

| Peak No. | 2θ[°] | d[Å] | relative intensity % |
|---|---|---|---|
| 1 | 10.60 | 8.3414 | 34.7 |
| 2 | 12.95 | 6.8297 | 20.4 |
| 3 | 14.24 | 6.2160 | 100.0 |
| 4 | 14.72 | 6.0142 | 14.5 |
| 5 | 15.88 | 5.5764 | 19.4 |
| 6 | 16.79 | 5.2766 | 41.4 |
| 7 | 17.54 | 5.0536 | 6.1 |
| 8 | 17.93 | 4.9444 | 30.5 |
| 9 | 18.41 | 4.8157 | 19.5 |
| 10 | 18.93 | 4.6831 | 7.9 |
| 11 | 19.44 | 4.5633 | 78.7 |
| 12 | 20.67 | 4.2927 | 6.5 |
| 13 | 21.24 | 4.1800 | 57.0 |
| 14 | 22.16 | 4.0091 | 13.3 |
| 15 | 22.80 | 3.8970 | 44.7 |
| 16 | 23.77 | 3.7400 | 46.9 |
| 17 | 24.57 | 3.6208 | 45.6 |
| 18 | 24.88 | 3.5754 | 12.9 |
| 19 | 25.32 | 3.5150 | 5.3 |
| 20 | 26.13 | 3.4081 | 7.7 |
| 21 | 27.24 | 3.2714 | 8.6 |
| 22 | 27.64 | 3.2246 | 5.5 |
| 23 | 28.15 | 3.1673 | 11.7 |
| 24 | 28.64 | 3.1138 | 11.6 |
| 25 | 29.33 | 3.0428 | 11.9 |
| 26 | 29.64 | 3.0116 | 27.1 |
| 27 | 30.16 | 2.9608 | 2.8 |
| 28 | 30.52 | 2.9265 | 3.0 |
| 29 | 31.48 | 2.8397 | 3.6 |
| 30 | 32.08 | 2.7879 | 9.5 |
| 31 | 32.73 | 2.7341 | 5.4 |
| 32 | 33.36 | 2.6837 | 29.7 |
| 33 | 34.36 | 2.6076 | 3.4 |

TABLE 6-continued

| Peak No. | 2θ[°] | d[Å] | relative intensity % |
|---|---|---|---|
| 34 | 35.36 | 2.5366 | 12.6 |
| 35 | 35.96 | 2.4953 | 7.3 |
| 36 | 36.24 | 2.4767 | 3.9 |
| 37 | 37.28 | 2.4097 | 3.9 |
| 38 | 38.28 | 2.3496 | 7.1 |
| 39 | 38.64 | 2.3283 | 6.4 |

Example 10 Stability Test

The crystal form A of the fumarate of the compound of formula (I) prepared in Example 9 and the crystal form 1 of the maleate of the compound of formula (I) prepared in Example 2 were placed in a 60° C. drying oven for different days (0 days, 7 days, 21 days). Samples were collected and detected to investigate the stability of the crystal forms. The results are shown in Table 7 below.

TABLE 7

| Sample | Experiment condition | Total impurity % | Content % |
|---|---|---|---|
| the crystal form A of the fumarate of the compound of formula (I) prepared in Example 9 | 0 day | 0.62 | 99.38 |
|  | 7 days | 0.69 | 99.31 |
|  | 21 days | 0.78 | 99.22 |
| the crystal form 1 of the maleate of the compound of formula (I) prepared in Example 2 | 0 day | 0.09 | 99.91 |
|  | 7 days | 0.12 | 99.88 |
|  | 21 days | 0.14 | 99.86 |
| the free base of the compound of formula (I) | 0 day | 0.50 | 99.50 |
|  | 7 days | 1.58 | 98.42 |
|  | 14 days | 2.56 | 97.44 |

The results show that the crystal form A of the fumarate of the compound of formula (I) and the crystal form 1 of the maleate of the compound of formula (I) have basically no change in content or in the characteristic peaks of the XRPD pattern after 21 days at high temperature, and the crystal forms are very stable.

The amorphous form of the free base of the compound of formula (I) was subjected to the same stability study as above-mentioned. The results show that the amorphous form of the free base of the compound of formula (I) has poor stability. The amorphous form has significant change in the character on the 7th and 14th day, it changes from a yellow solid to a hard gelatinous substance with more types of impurities and increased content of the impurities.

Example 11 Solubility Test

Weigh about 50 mg of the crystal form 1 of the maleate of the compound of formula (I) prepared in Example 2, which was added into different bottles. Then PBS buffers with different pH values were prepared. Each of them was added in batches with a small amount into each of the above bottles at room temperature till the crystal form in each bottle was just dissolved. The total amount of the solvent was recorded and the solubility was calculated. The results are shown in Table 8 below.

TABLE 8

| Sample | Experiment condition | Solubility (S, mg/mL) |
|---|---|---|
| the crystal form 1 of the maleate of the compound of formula (I) | PBS 6.0 | 41 |
|  | PBS 6.5 | 45 |
|  | PBS 7.0 | 57 |
|  | PBS7.5 | 62 |
|  | water | 31 |
|  | normal saline | 50 |

The amorphous form of the free base of the compound of formula (I) was subjected to the same solubility study as above-mentioned. It was found that the free base of the compound of formula (I) had significant lower solubility under the same experiment conditions, especially a very low solubility in water, which was shown in Table 9.

TABLE 9

| Sample | Experiment condition | Solubility (S, mg/mL) |
|---|---|---|
| the free base of the compound of formula (I) | PBS pH = 6.5 | about 15.10 |
|  | PBS pH = 7.0 | about 12.5 |
|  | PBS pH = 7.2 | about 10.10 |
|  | PBS pH = 7.5 | about 0.44 |
|  | water | about 0.1 |

The results show that the solubility of the crystal form 1 of the maleate of the compound of formula (I) in each of the above-mentioned solvents is significantly improved, and the solubility can reach 30-60 mg/mL, which greatly improves the solubility of the compound of formula (I).

Example 12 Hygroscopicity Test

Experimental method: this test was carried out by a dynamic moisture adsorption instrument. Weigh 10 mg of a solid sample, which was placed on a balance. The humidity in the sample room was controlled through the program. The sample was placed under the same temperature and different humidity conditions for 7 days, then the quality change of the tested sample was measured with relative humidity. Detection procedure: the humidity change was 0%-95%-0%; the test temperature was 25° C.

Figure 15:
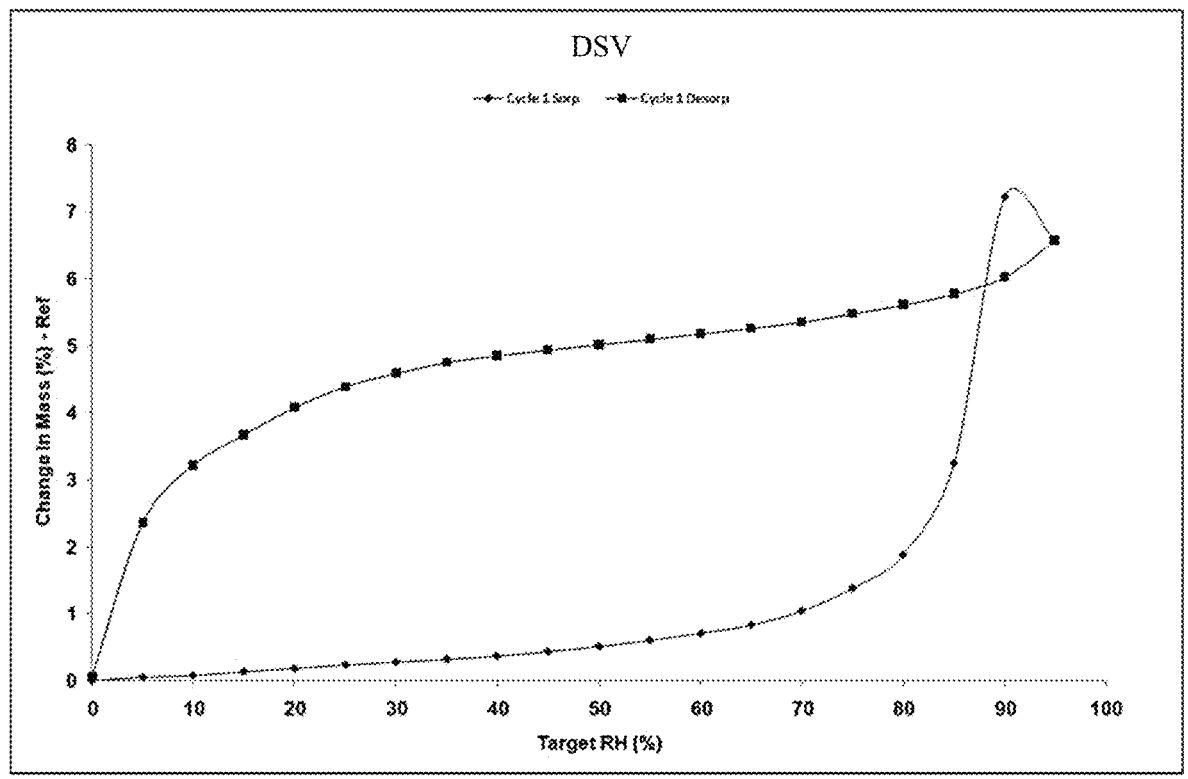
FIG. 15 is a DVS spectrum of the crystal form 1 of the maleate of the compound of formula (I) prepared in Example 2.
Figure 16:
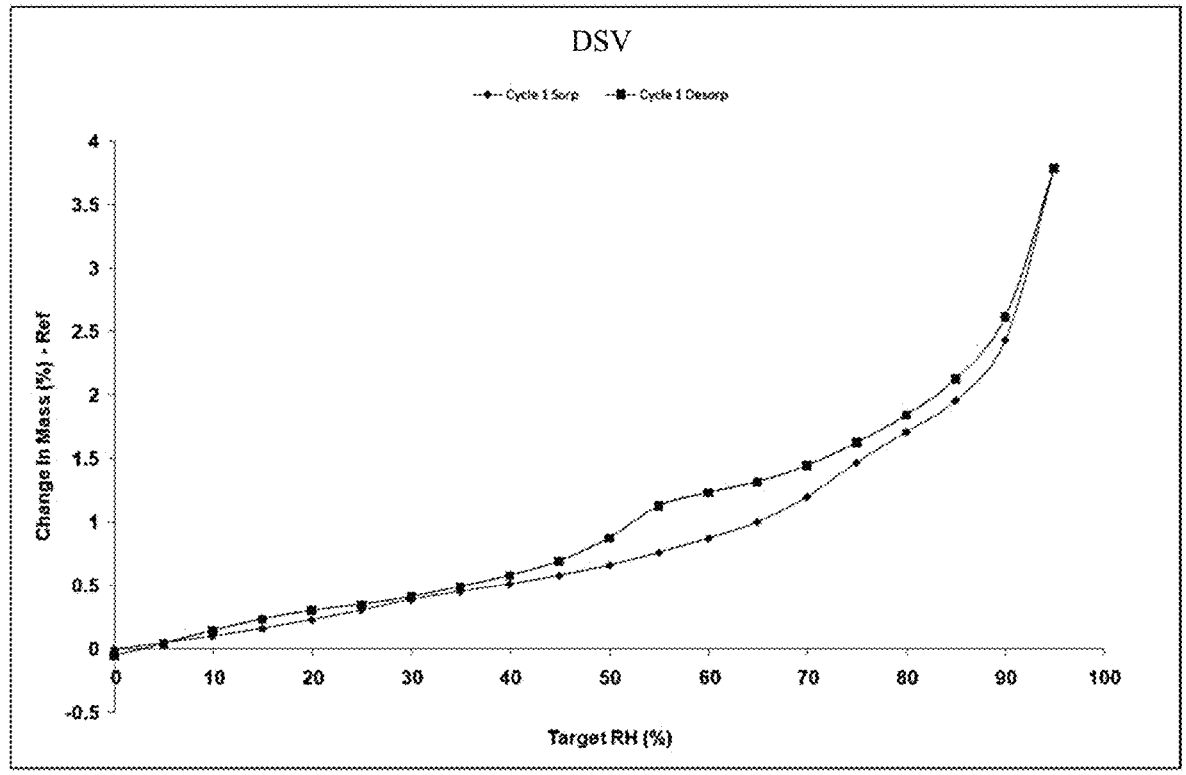
FIG. 16 is a DVS spectrum of the crystal form A of the fumarate of the compound of formula (I) prepared in Example 9.

The experimental results are shown in FIG. 15 (for the crystal form 1 of the maleate of the compound of formula (I) prepared in Example 2) and FIG. 16 (for the crystal form A of the fumarate of the compound of formula (I) prepared in Example 9). The results show that the two types of salts have similar hygroscopicity. Under the environment humidity of RH=60%, the weight increasement due to moisture absorption is about 1%, and the hygroscopicity is weak, which is obviously better than that of the free base state.

Figure 20:
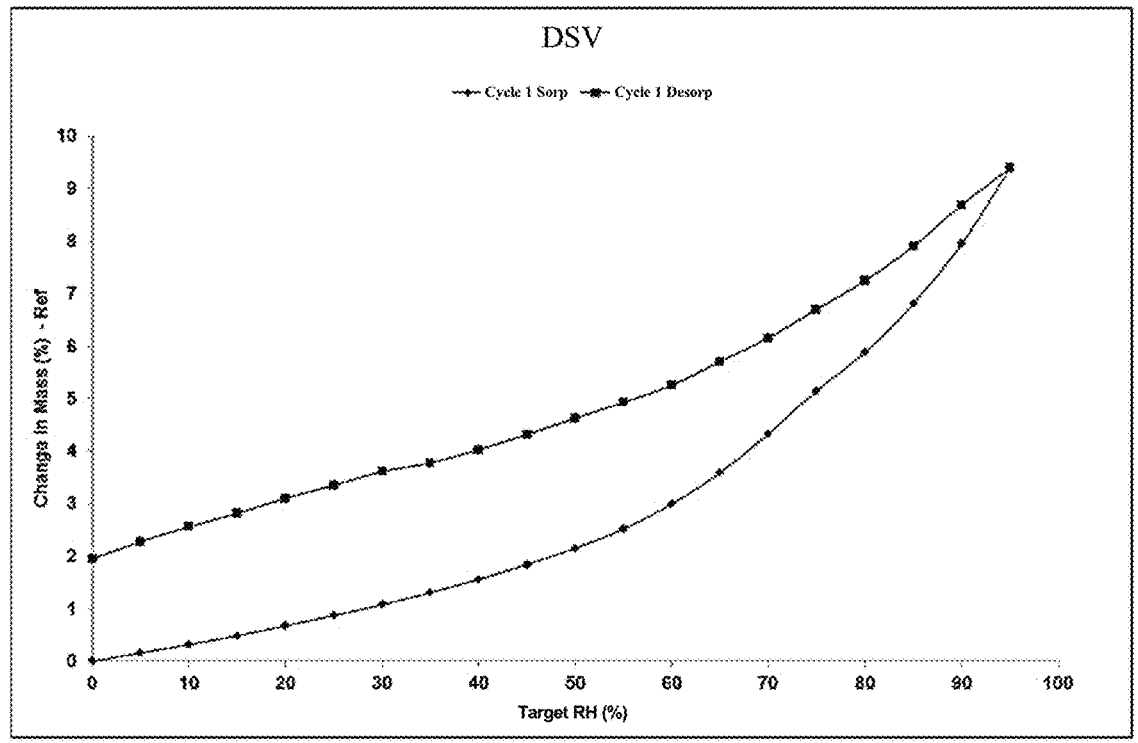
FIG. 20 is a DVS spectrum of the free base of the compound of formula (I).

The amorphous form of the free base of the compound of formula (I) was subjected to the same hygroscopicity study as above-mentioned. It is found that the amorphous form of the free base of the compound of formula (I) has poor stability. Under the environment humidity of higher than 60%, it shows quite strong hygroscopicity and the properties of the sample after moisture absorption are significantly changed (existing agglomeration phenomenon). The DVS test was carried out and the result is shown in FIG. 20. It can be seen that the amorphous of the free base of the compound of formula (I) has quite strong hygroscopicity and will absorb moisture persistently as the environmental humidity increases. When the relative humidity is 95%, the weight increasement due to moisture absorption can reach 9.5%, and the sample after moisture absorption is not easy to desorb.

Example 13 Stability Study

The crystal form 2 of the maleate of the compound of formula (I) prepared in Example 3 was placed in a 60° C. drying oven, and samples were taken and tested for different days (0 days, 7 days, 14 days and 30 days) to investigate the stability of the crystal form. The result is shown in Table 10.

TABLE 10

| Sample | Experiment condition | Total impurity % | Content % |
|---|---|---|---|
| the crystal form 2 | 0 day | 0.87 | 99.13 |
| | 7 days | 1.44 | 98.56 |
| | 14 days | 2.27 | 97.73 |

The results showed that the characteristic peaks of the XRPD pattern of the crystal form 2 are basically unchanged after 14 days at high temperature, and the crystal form is very stable, which is the original crystal form.

Example 14 Biological Experiment

Weigh 5.61 mg of the crystal form 1 of the maleate of the compound of formula (I) prepared in Example 2, which was dissolved it in 74.7 µL of DMSO. The solution had a concentration of 100 mM, and was stored in a refrigerator at −20° C.

Configure 1000× compound storage plate (or called 1000× storage medicine plate): the 100 mM compound storage solution was diluted with DMSO. The starting concentration was 10 mM and 9 concentration gradients (th concentration of the storage solution was 10 mM, 3 mM, 1 mM, 0.3 mM, 0.1 mM, 0.03 mM, 0.01 mM, 0.001 mM and 0.0001 mM respectively) were set. The compound storage plate was sealed with a sealing tape, and stored in a refrigerator at −20° C. for later use.

Acute myeloid leukemia cells MV-4-11 (purchased from ATCC) were selected and seaded into a 96-well plate (140 µL per well) at a density of 5000/well and cultured overnight in a incubator with 37° C., 5% $CO_2$.

1000×storage medicine plates were taken out and melt at room temperature while avoiding light. Then prepare 15× intermediate medicine plates (78.8 µL of medium and 1.2 µL of medicine-containing DMSO storage solution), which were mixed well. 10 µL of the medicine-contained medium (15×) was added into the 96-well cell plates (the final concentration was 10 µM, 3 µM, 1 µM, 0.3 µM, 0.1 µM, 0.03 µM, 0.01 µM, 0.001 µM and 0.0001 µM, respectively, and the final concentration of DMSO was 0.01%), which were gently patted to well-mixed, then put it in a incubator with 37° C., 5% $CO_2$, and continued to incubate for 24 hours.

Then the CellTiter-Glo method was used to detect vitality of the cell under the conditions of each drug concentration, and the rate of cell proliferation inhibition under the corresponding conditions was calculated.

On MV-4-11 cells, the crystal form 1 of the maleate of the compound of formula (I) has no significant changes in cell growth within the concentration range of 0.0001 µM to 0.01 µM, and has a significant inhibitory effect on cell growth within the concentration range of 0.03 µM to 10 µM. The absolute half inhibitory concentration ($ABsIC_{50}$) of the crystal form 1 of the maleate of the compound of formula (I) on MV-4-11 cells is 0.032 µM.

Comparative Example 1

Similarly, by using the method described in Example 1 or Example 9, the according salts of the compound of formula (I) were prepared with the citric acid, L-tartaric acid, sulfuric acid or phosphoric acid instead of the maleic acid or the fumaric acid. As a result, it is found that no solid in crystal form is obtained at all after salting citric acid, tartaric acid, sulfuric acid or phosphoric acid with the compound of formula (I).

Comparative Example 2

Similarly, by using the method described in Example 1 or Example 9, the according salt of the compound of formula (I) were prepared with the hydrochloric acid instead of the maleic acid or the fumaric acid. As a result, it is found that although a solid in crystal form was obtained after salting with hydrochloric acid, the hydrochloride of the compound of formula (I) is very hygroscopic and cannot be used in subsequent applications.

Comparative Example 3

The amorphous of the free base of the compound of formula (I) was subjected to crystallization through methods such as volatilization, cooling, and solventing-out. As a result, no good crystal morphology is obtained.

Volatilization: the solution obtained by completely dissolving the free base of the compound of formula (I) with the solvent shown in Table 11 was placed in a vacuum oven at 250° C. and volatilized under vacuum (0.1 MPa) for 7 days. As a result, it is found that the obtained substances are all oily gums. These oily gums were re-dissolved by adding the corresponding equal amount of the same solvent, and then volatilized naturally at room temperature (T=20±2° C.). As a result, it is found that no good solid sample is obtained.

TABLE 11

| Solvent | Firsly volatilized | Experimental operation | Experimental phenomenon (23 days) |
|---|---|---|---|
| Methanol | oily gum | re-dissolved and volatilized naturally at room temperature | oily |
| Ethanol | oily gum | re-dissolved and volatilized naturally at room temperature | oily |
| Isopropanol | oily gum | re-dissolved and volatilized naturally at room temperature | oily |
| acetone | oily gum | re-dissolved and volatilized naturally at room temperature | oily |

TABLE 11-continued

| Solvent | Firsly volatilized | Experimental operation | Experimental phenomenon (23 days) |
|---|---|---|---|
| 2-butanone | oily gum | re-dissolved and volatilized naturally at room temperature | oily |
| Tetrahydrofuran | oily gum | re-dissolved and volatilized naturally at room temperature | oily |
| Ethyl acetate | oily gum | re-dissolved and volatilized naturally at room temperature | oily |
| Isopropyl acetate | oily gum | re-dissolved and volatilized naturally at room temperature | oily |
| Dichloromethane | oily gum | re-dissolved and volatilized naturally at room temperature | oily |
| Dimethyl sulfoxide | oily gum | re-dissolved and volatilized naturally at room temperature | liquid |
| N,N-Dimethylformamide | oily gum | re-dissolved and volatilized naturally at room temperature | liquid |
| N-methylpyrrolidone | oily gum | re-dissolved and volatilized naturally at room temperature | liquid |
| Acetonitrile | oily gum | re-dissolved and volatilized naturally at room temperature | oily |

Cooling: Weigh about 50 mg of the free base of the compound of formula (I) which was added into each bottle and dissolved by adding 1 mL of the different solvent in Table 12 at room temperature (T=20° C.). After the solutions were kept at 0° C. for 2 hours, it was recorded whether a solid precipitated, and after the solutions were further cooled to −20° C. and then kept overnight, it was recorded whether a solid precipitated. The results are shown in Table 12. It is found that no good solid sample could be obtained after cooling.

TABLE 12

| Solvent | whether a solid precipitates at 0° C. | whether a solid precipitates at −20° C. |
|---|---|---|
| Methanol | No | No |
| Ethanol | No | No |
| Isopropanol | No | No |
| Acetone | No | No |
| 2-butanone | No | No |
| Tetrahydrofuran | No | No |
| Ethyl acetate | No | Very few amount |
| Isopropyl acetate | No | No |
| Dichloromethane | No | No |
| Dimethyl sulfoxide | No | No |
| N,N-Dimethylformamide | No | No |
| N-methylpyrrolidone | No | No |
| Acetonitrile | No | Very few amount | solventing-out: Weigh about 50 mg of the free base of the compound of formula (I), which was added into each bottle and dissolved by adding 1 mL of the different solvent in Table 12 at room temperature (T=20° C.). After the addition of a certain amount of anti-solvent (slowly adding dropwise), it was observed whether a solid precipitated. The results are shown in Table 13. It is found that no good solid sample could be obtained after adding anti-solvent.

TABLE 13

| Solvent | Anti-solvent | Solvent amount (ml) | whether a solid precipitates |
|---|---|---|---|
| Methanol | MTBE(not soluble with cyclohexane) | 3 | No |
| Ethanol | Cyclohexane | 3 | No |
| Isopropanol | Cyclohexane | 3 | No |
| Acetone | Water | 2 | Oil precipitates |
| 2-butanone | Water (not soluble with cyclohexane) | 3 | No |
| Tetrahydrofuran | Cyclohexane | 3 | No |
| Ethyl acetate | Cyclohexane | 3 | No |
| Isopropyl acetate | Cyclohexane | 3 | No |
| Dichloromethane | Cyclohexane | 2 | Oil precipitates |
| Dimethyl sulfoxide | Water | 2 | Oil precipitates |
| N,N-Dimethylformamide | Water | 2.7 | Oil precipitates |
| N-methylpyrrolidone | Water | 3 | Oil precipitates |
| Acetonitrile | Water | 2.5 | Oil precipitates |

It can be seen that through a large number of experimental studies, the inventors have discovered crystal forms of the compound of formula (I) which are very stable and good in several related properties, which are the crystal form I, crystal form 1, crystal form 2, crystal form 3 and crystal form 4 of its maleate and the crystal form A of its fumarate.

Example 15 Pharmaceutical Composition

Tablets of the crystal form 1 were prepared from the following components:

| | |
|---|---|
| The crystal form 1 of the maleate of the compound of formula (I) prepared in Example 2 | 20 g |
| Starch | 20 g |
| Lactose | 20 g |
| PVPP | 3 g |
| PVP | 3 g |
| Talc | 1.6 g |
| Sodium lauryl sulfate | 5 g |

According to the conventional method, the crystal form 1 of the maleate of the compound of formula (I) was mixed with starch, sieved and then mixed with other components uniformly, and directly compressed into tablets.

Example 16 Pharmaceutical Composition

Tablets of the crystal form A were prepared from the following components:

| | |
|---|---|
| The crystal form A of the fumarate of the compound of formula (I) prepared in Example 9 | 20 g |
| Starch | 20 g |
| Lactose | 20 g |
| PVPP | 3 g |
| PVP | 3 g |
| Talc | 1.6 g |
| Sodium lauryl sulfate | 5 g |

According to the conventional method, the crystal form A of the fumarate of the compound of formula (I) was mixed with starch, sieved and then mixed with other components uniformly, and directly compressed into tablets.

All documents mentioned in the present invention are cited as references in this application, as if each document was individually cited as a reference. In addition, it should be understood that after reading the above teaching content of the present invention, those skilled in the art can make various changes or modifications to the present invention, and these equivalent forms also fall within the scope defined by the appended claims of the present application.

What is claimed is:

1. A polymorph of a maleate or fumarate salt of a compound of formula (I)

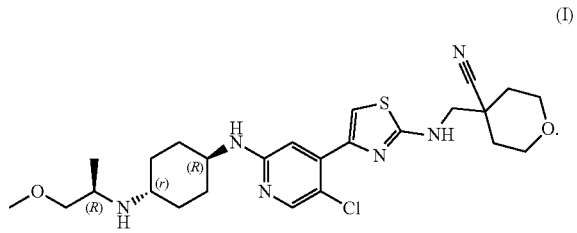

(I)

2. The polymorph according to claim 1, wherein the polymorph is the maleate salt of the compound of formula (I), and wherein the molar ratio of the compound of formula (I) to the maleic acid is 1:2.

3. The polymorph according to claim 2, wherein the polymorph is crystal form 1 of the maleate salt of the compound of formula (I), and the X-ray powder diffraction pattern of the crystal form 1 comprises diffraction angle 2θ (°) values selected from the group consisting of: 5.48±0.2°, 14.26±0.2°, 19.68±0.2°, and 22.44±0.2°.

4. The polymorph according to claim 3, wherein the differential scanning calorimetry analysis spectrum of the crystal form 1 has a characteristic peak at 162.45±5° C.

5. The polymorph according to claim 2, wherein the polymorph is crystal form 2 of the maleate salt of the compound of formula (I), and the X-ray powder diffraction pattern of the crystal form 2 comprises diffraction angle 2θ (°) values selected from the group consisting of: 5.02±0.2°, 5.36±0.2°, 14.04±0.2°, 20.96±0.2°, 21.42±0.2°, and 23.00±0.2°.

6. The polymorph according to claim 5, wherein the differential scanning calorimetry analysis spectrum of the crystal form 2 has a characteristic peak at 159.25±5° C.

7. The polymorph according to claim 3, wherein the polymorph is crystal form 3 of the maleate salt of the compound of formula (I), and the X-ray powder diffraction pattern of the crystal form 3 comprises diffraction angle 2θ (°) values selected from the group consisting of: 5.64±0.2°, 11.28±0.2°, 16.96±0.2°, and 24.92±0.2°.

8. The polymorph according to claim 7, wherein the differential scanning calorimetry analysis spectrum of the crystal form 3 has a characteristic peak at 114.72±5° C.

9. The polymorph according to claim 2, wherein the polymorph is crystal form 4 of the maleate salt of the compound of formula (I), and the X-ray powder diffraction pattern of the crystal form 4 comprises diffraction angle 2θ) (° values selected from the group consisting of: 5.08±0.2°, 5.62±0.2°, 13.98±0.2°, and 22.72±0.2°.

10. The polymorph according to claim 9, wherein the differential scanning calorimetry analysis spectrum of the crystal form 4 has a characteristic peak at 175.74+5° C.

11. The polymorph according to claim 2, wherein the polymorph is crystal form I of the maleate salt of the compound of formula (I), and the X-ray powder diffraction pattern of the crystal form I comprises diffraction angle 2θ (°) values selected from the following group consisting of: 5.00±0.2°, 5.40±0.2°, 14.23±0.2°, 22.40±0.2°, and 23.28±0.2°.

12. The polymorph according to claim 11, wherein the differential scanning calorimetry analysis spectrum of the crystal form I has a characteristic peak at 159.91±5° C.

13. The polymorph according to claim 1, wherein the polymorph is the fumarate salt of the compound of formula (I), and wherein the molar ratio of the compound of formula (I) to the fumaric acid is 2:1.

14. The polymorph according to claim 13, wherein the polymorph is crystal form A of the fumarate salt of the compound of formula (I), and the X-ray powder diffraction pattern of the crystal form A comprises diffraction angle 2θ (°) values selected from the group consisting of: 14.24±0.2°, 19.44±0.2°, 21.24±0.2°, 23.77±0.2°, and 24.57±0.2°.

15. The polymorph according to claim 14, wherein the differential scanning calorimetry analysis spectrum of the crystal form A has a characteristic peak at 218.67±5° C.

16. A pharmaceutical composition comprising the polymorph according to claim 1 and a pharmaceutically acceptable carrier.

17. A method for the prevention or treatment of a CDK9-related disease, comprising the step of administering to a subject in need thereof a therapeutically effective amount of the polymorph according to claim 1.

18. The method of claim 17, wherein the CDK9-related disease is cancer.

19. A method for preparing a polymorph of a maleate or fumarate salt of a compound of formula (I);

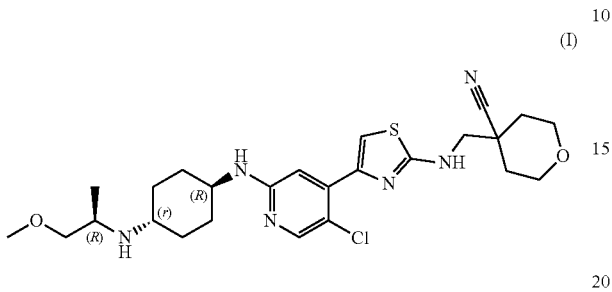

(I)

wherein;

(A) the polymorph is crystal form I of the maleate salt of the compound of formula (I) and the X-ray powder diffraction pattern of the crystal form I comprises diffraction angle 2θ (°) values selected from the group consisting of: 5.00±0.2°, 5.40±0.2°, 14.23±0.2°, 22.40±0.2°, and 23.28±0.2°; and the method comprises the step of: (1) the compound of formula (I) and maleic acid are stirred in an organic solvent to form the crystal form I of the maleate salt of the compound of formula (I); wherein the molar ratio of the compound of formula (I) to the maleic acid is 1:2;

or (B) the polymorph is crystal form 1 of the maleate salt of the compound of formula (I) and the X-ray powder diffraction pattern of the crystal form 1 comprises diffraction angle 2θ (°) values selected from the group consisting of: 5.48±0.2°, 14.26±0.2°, 19.68±0.2°, and 22.44±0.2°; and the method comprises the steps:

(1) the compound of formula (I) and maleic acid are stirred in an organic solvent to form the maleate salt of the compound of formula (I); wherein the molar ratio of the compound of formula (I) to the maleic acid is 1:2;

(2a) the maleate salt of the compound of formula (I) obtained in step (1) is dissolved in a first crystallization solvent to obtain a solution containing the maleate salt of the compound of formula (I); and (3a) the solution obtained in step (2a) is crystallized, and filtered after the crystallization, and the solid is collected to obtain the crystal form 1 of the maleate salt of the compound of formula (I);

or (C) the polymorph is crystal form 2 of the maleate salt of the compound of formula (I) and the X-ray powder diffraction pattern of the crystal form 2 comprises diffraction angle 2θ (°) values selected from the group consisting of: 5.02±0.2°, 5.36±0.2°, 14.04±0.2°, 20.96±0.2°, 21.42±0.2°, and 23.00±0.2°; and the method comprises the steps:

(1) the compound of formula (I) and maleic acid are stirred in an organic solvent to form the maleate salt of the compound of formula (I); wherein the molar ratio of the compound of formula (I) to the maleic acid is 1:2; and (2b) the maleate salt of the compound of formula (I) obtained in step (1) is stirred in a second crystallization solvent at 0-50° C., filtered, and the solid is collected to obtain the crystal form 2 of the maleate salt of the compound of formula (I);

or (D) the polymorph is crystal form 3 of the maleate salt of the compound of formula (I) and the X-ray powder diffraction pattern of the crystal form 3 comprises diffraction angle 2θ (°) values selected from the group consisting of: 5.64±0.2°, 11.28±0.2°, 16.96±0.2°, and 24.92+0.2°; and the method comprises the steps:

(1) the compound of formula (I) and maleic acid are stirred in an organic solvent to form the maleate salt of the compound of formula (I); wherein the molar ratio of the compound of formula (I) to the maleic acid is 1:2; and (2c) the maleate salt of the compound of formula (I) obtained in step (1) is stirred in a third crystallization solvent at 45-55° C., filtered, and the solid is collected to obtain the crystal form 3 of the maleate salt of the compound of formula (I);

or (E) the polymorph is crystal form 4 of the maleate salt of the compound of formula (I) and the X-ray powder diffraction pattern of the crystal form 4 comprises diffraction angle 2θ (°) values selected from the group consisting of: 5.08±0.2°, 5.62±0.2°, 13.98±0.2°, and 22.72±0.2°; and the method comprises the steps:

(1) the compound of formula (I) and maleic acid are stirred in an organic solvent to form the maleate salt of the compound of formula (I); wherein the molar ratio of the compound of formula (I) to the maleic acid is 1:2; and (2d) the maleate salt of the compound of formula (I) obtained in step (1) is stirred in a fourth crystallization solvent at 20-60° C., filtered, and the solid is collected to obtain the crystal form 4 of the maleate salt of the compound of formula (I);

or (F) the polymorph is crystal form A of the fumarate of the compound of formula (I) and the X-ray powder diffraction pattern of the crystal form A comprises diffraction angle 2θ (°) values selected from the group consisting of: 14.24±0.2°, 19.44±0.2°, 21.24±0.2, and 23.77±0.2°, 24.57±0.2°; wherein the molar ratio of the compound of formula (I) to the fumaric acid is 2:1; and the method comprises the steps:

(a) the compound of formula (I) and fumaric acid are stirred in an organic solvent at 40-60° C.; and (b) the mixed system is cooled to 10-30° C., filtered, and the solid is collected to obtain the crystal form A of the fumarate salt of the compound of formula (I).

20. A method for the treatment of a CDK9-related disease, comprising the step of administering to a subject in need thereof a therapeutically effective amount of the pharmaceutical composition according to claim 16.

21. A method for the prevention of a CDK9-related disease, comprising the step of administering to a subject in need thereof a therapeutically effective amount of the pharmaceutical composition according to claim 16.

* * * * *